United States Patent [19]
Rolfe et al.

[11] Patent Number: 5,137,816
[45] Date of Patent: Aug. 11, 1992

[54] **RHIZOBIAL DIAGNOSTIC PROBES AND *RHIZOBIUM TRIFOLII* NIFH PROMOTERS**

[75] Inventors: Barry G. Rolfe, Curtin; John Shine, Sydney; Kieran F. Scott, Page; John M. Watson, Holder, all of Australia; Peter Schofield, Heidelberg, Fed. Rep. of Germany

[73] Assignee: The Lubrizol Corporation, Wickliffe, Ohio

[21] Appl. No.: 701,358

[22] Filed: May 10, 1991

Related U.S. Application Data

[63] Continuation of Ser. No. 109,870, Oct. 16, 1987, abandoned, and a continuation-in-part of Ser. No. 662,611, Oct. 23, 1984, abandoned, which is a continuation of Ser. No. 554,984, Nov. 23, 1983, abandoned, said Ser. No. 109,870, is a continuation-in-part of Ser. No. 900,270, Aug. 26, 1986, abandoned, which is a continuation-in-part of Ser. No. 506,676, Jun. 22, 1983, abandoned.

[51] Int. Cl.$^5$ .......... C12N 15/00; C12N 1/20; C12R 1/41; C07H 15/12
[52] U.S. Cl. .............. 435/172.3; 435/252.2; 435/252.3; 435/320.1; 435/878; 536/27; 935/41; 935/72
[58] Field of Search ............... 435/172.3, 252.2, 252.3, 435/320.1, 878; 536/27; 935/41, 72

[56] References Cited

FOREIGN PATENT DOCUMENTS

83/01073  3/1983  World Int. Prop. O. .

OTHER PUBLICATIONS

Kaluza et al. 1985. FEBS Letters 188(1): 37–42.
Scott et al. 1983. DNA 2:149–154.
Ruvkun et al. 1980. Proc. Natl. Acad. Sci. USA: 77(1):191–195.
Torok et al. 1981. Nucl. Acids. Res. 9(21):5711–5723.
Schofield, P. R. et al. (1984) Plant Mol. Biol. 3:3–11.
Watson, J. M. and Schofield, P. R. (1985) Mol. Gen. Genet. 199:279–289.
Schofield, P. R. and Watson, J. M. (1985) Nucl. Acids Res. 13:3407–3418.
Nayudu, M. and Rolfe, B. G. (1987) Mol. Gen. Genet. 206:326–337.
Shine, J. et al. (1984) Chemical Abstracts 100(15):122–ref. No. 115662t.
Watson, J. M. et al. (1984) Chemical Abstracts 100(15):136–ref. no. 115797r.
Ditta, G. et al. (1984) Chemical Abstracts 100(11):109–ref. no. 80500j.
Watson, J. M. et al. (1987) Chemical Abstracts 106(7)–ref. no. 44782t.
Wirth, D. F. et al. (1982) Proc. Natl. Acad. Sci. USA 79:6999–7003.
Sprent, J. I. (1979) The Biology Of Nitrogen Fixing Organisms, McGraw-Hill, London, pp. 8–11.

(List continued on next page.)

*Primary Examiner*—David T. Fox
*Attorney, Agent, or Firm*—Greenlee and Associates

[57] ABSTRACT

This invention provides useful promoters from the *R. trifolii* nifH gene for the construction of recombinant molecules to regulate foreign genes for expression under desired conditions. In particular, the promoters act to control expression of the foreign genes within root nodules formed by rhizobial bacterial strains in symbiotic combination with host plants.

A rhizobium diagnostic segment (RDS) is also provided comprising a DNA segment found at more than one location in rhizobia, the RDS being species-specific, and detectable by DNA hybridization under stringent conditions. A recombinant plasmid comprising a RDS and a bacterial strain containing the plasmid are provided. Methods are provided for identifying species and strains of field isolates of Rhizobium, using RDS's. One RDS exemplified comprises 5' sequences from the *R. trifolii* nifH gene.

7 Claims, 2 Drawing Sheets

OTHER PUBLICATIONS

Burns, R. C. and Hardy, R. W. F. (1975) Nitrogen Fixation in Bacteria and Higher Plants, Springer-Verlag, Berlin.

Vincent, J. M. (1980) in Symbiotic Associations and Cyanobacteria, Nitrogen Fixation, vol. 2, W. E. Newton, W. H. Orme-Johnson (eds.), University Park Press, Baltimore, pp. 103-129.

Jordan, D. C. (1982) Int. J. Syst. Bacteriol. 32:136-139.

Scott, K. F. (1986) Nucl. Acids Res. 14:2905-2919.

Bohlool, B. B. and Schmidt, E. L. (1974) Science 185:269-271.

Vincent, J. M. et al. (1979) in "Identification Methods for Microbiologists," F. A. Skinner & D. W. Lovelock (eds.) Academic Press, London.

Vincent, J. M. (1982) in "Nitrogen Fixation in Legume," Academic Press, New York, pp. 5-11.

Vincent, J. M. (1970) "A Manual for the Practical Study of Root-Nodule Bacteria," IBP Handbook No. 15, Blackwell Scientific Publications, Oxford.

Lieberman, M. T. et al. (1985) Plant Soil 84:225-244.

Hooykaas, P. J. J. et al. (1981) Nature 291:351.

Southern, E. M. (1975) J. Mol. Biol. 98:503-517.

Maxam, A. M. and Gilbert, W. (1980) Methods Enzymol. 65:499-560.

Shine, J. and Dalgarno, L. (1975) Nature 254:34-38.

Schwinghamer, E. A. (1964) Can. J. Microbiol. 10:221-233.

Schwinghamer, E. A. (1967) Antonie van Leeuwenhock 33:121-136.

Lippman, D. J. and Pearson, W. R. (1985) Science 227:1435-1441.

Better, M. et al. (1983) Cell 35:479-485.

Sundaresan, V. et al. (1983) Nature 301:728-732.

Hodgson A. L. M. and Roberts, W. P. (1983) J. Gen. Microbiol. 129:207-212.

Jarvis B. D. W. et al. (1980) Int. J. Syst. Bacteriol. 30:42-52.

Jarvis B. D. W. et al. (1986) Int. J. Syst. Bacteriol. 36:129-138.

RHIZOBIAL DIAGNOSTIC PROBES AND *RHIZOBIUM TRIFOLII* NIFH PROMOTERS

CROSS-REFERENCE TO RELATED APPLICATIONS

This application is a continuation of copending application Ser. No. 109,870 filed Oct. 16, 1987, now abandoned, which is a continuation-in-part application of application Ser. No. 662,611 filed Oct. 23, 1984, now abandoned, which is a continuation-in-part of abandoned application Ser. No. 554,984 filed Nov. 23, 1983; and is a continuation-in-part application of copending application Ser. No. 900,270 filed Aug. 26, 1986, now abandoned, which is a continuation of abandoned application Ser. No. 506,676 filed Jun. 22, 1983, all of the foregoing applications being incorporated herein by reference.

FIELD OF THE INVENTION

This application lies in the field of recombinant DNA techniques applied to bacteria, specifically DNA probes useful for identifying rhizobial species and strains.

BACKGROUND OF THE INVENTION

Biological nitrogen fixation in the root nodules of leguminous plants is a major component of world food production and therefore practical applications of this field are of major interest.

Prokaryotes can use a wide variety of nitrogen compounds as sole sources of cellular nitrogen. This variety includes ammonia, dinitrogen and nitrate among the inorganic compounds, and proline, arginine and glutamine among complex organic compounds. Each species can utilize a different array of nitrogen compounds. Glutamine, glutamate and aspartate are the key nitrogen compounds in intermediary metabolism. The latter two are the starting compounds of many pathways of amino acid biosynthesis and serve as amino group donors in many reactions. In all other cases the amino group is donated by glutamine. The major enzyme required for the assimilation of ammonia is glutamine synthetase, which catalyses the reaction:

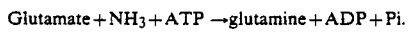

Glutamate + $NH_3$ + ATP → glutamine + ADP + Pi.

Utilization of the assimilated ammonia depends on the activity of glutamate synthase catalyzing:

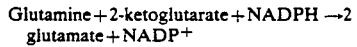

Glutamine + 2-ketoglutarate + NADPH → 2 glutamate + $NADP^+$

Since ATP is hydrolysed, these reactions have a favorable equilibrium and allow the use of ammonia in the medium or ammonia derived enzymatically from other nitrogen sources (Meers, J., Tempest, D. and C. Brown (1970) J. Gen. Microbiol. 64:187-194). The formation of ammonia is thus a key step in the biological nitrogen cycle.

Biological nitrogen fixation can be achieved by a variety of microorganisms and occurs through the induction of an enzyme complex, nitrogenase, which converts atmospheric nitrogen to ammonia. This conversion occurs in a group of physiologically diverse prokaryotes, including facultative anaerobes (e.g., *Klebsiella pneumoniae*) obligate aerobes (e.g., *Azotobacter vinelandii*), photosynthetic bacteria (e.g., *Rhodospirillum rubrum*), and some strains of blue-green algae (e.g., *Anabaena cylindrica*). (Sprent, J. I. (1979) The biology of nitrogen fixing organisms, London, McGraw-Hill, pp. 8-11). While this enzyme complex is common to all characterized nitrogen fixing organisms, the conditions under which it is expressed vary considerably between species (Burns, R. C., Hardy, R. W. F. (1975): Nitrogen fixation in bacteria and higher plants, Springer-Verlag, Berlin).

The first stages of nitrogen fixation, conversion of nitrogen into ammonia, are achieved symbiotically in the root nodules of leguminous plants which contain the nitrogen-fixing bacteria of the genera Rhizobium and Bradyrhizobium (hereinafter referred to as "rhizobial species"). Some non-leguminous plants, e.g., alder, also have interactions with symbiotic bacteria which are nitrogen fixers. In addition, free-living bacteria, e.g., *Klebsiella pneumoniae* and the photosynthetic blue-green bacteria, also fix nitrogen.

The symbiotic association between plants and bacteria of rhizobial species is the result of a complex interaction between the bacterium and its host, requiring the expression of both bacterial and plant genes in a tightly coordinated manner (Vincent, J. M. (1980) In Symbiotic Associations and Cyanobacteria, Nitrogen Fixation, Vol. 2 (W. E. Newton, W. H. Orme-Johnson, eds.) Baltimore, University Park Press pp. 103-129; and Verma, D. P. S., Legocki, R. P. and S. Auger (1981) In Current Perspectives in Nitrogen Fixation (A. H. Gibson, W. E. Newton, eds.) Canberra: Australian Academy of Science, pp. 205-208). In free-living rhizobial species, nitrogenase synthesis is repressed and is only induced after the symbiotic relationship has been established. Furthermore, some rhizobial species only interact with a narrow range of plant species, whereas other species interact with a wide range.

Bacteria bind to the emerging plant root hairs and invade the root tissue through the formation of an infection thread. The plant responds to this infection by the development of a highly differentiated root nodule. These nodules are the site of synthesis of the nitrogenase complex. Following nitrogen fixation, the fixed nitrogen is exported into the plant tissue and assimilated by the plant-derived enzymes (Scott, D. B., Farnden, K. J. F. and Robertson, J. G. (1976) Nature 263:703-705).

Most rhizobial symbioses are confined to leguminous plants. Furthermore, rhizobial strains which fix nitrogen in association with the agriculturally-important temperate legumes are usually restricted in their host range to a single legume genus. However, some rhizobial strains have been isolated which can fix nitrogen in a diverse group of legume species but can also form an effective symbiosis with non-legumes.

Early literature references to *Rhizobium japonicum* refer to strains characterized as "slow-growing" Rhizobia. More recent studies of biochemical and genetic characteristics have led to reclassification of "slow-growing" Rhizobia in the genus Bradyrhizobium (Jordan, D. C. (1982) Int. J. Syst. Bacteriol. 32:136). Furthermore, certain "fast-growing" strains have been found which are classified as *R. japonicum* on the basis of their ability to nodulate *Glycine Max* cv. Peking, an undeveloped Asian cultivar of soybean. Since the literature sometimes refers to slow-growing (Bradyrhizobium) strains simply as *R. japonicum*, confusion may occur. For clarity herein, "slow-growing" soybean nodulating strains are termed *Bradyrhizobium japonicum* strains, while "fast-growing" strains are termed *Rhizo-*

*bium japonicum* strains. Similarly, *Parasponia Rhizobium* sp. has been reclassified as Bradyrhizobium sp. (Parasponia) (see, e.g. Scott, K. F. (1986), "Conserved nodulation genes from the non-legume symbiont Bradyrhizobium sp. (Parasponia)," Nucl. Acids Res. 14:2905-2919), and will be so referred to herein, although prior art references may specify the former name.

In some cases, e.g., *Klebsiella pneumoniae*. free-living bacteria can carry out the reduction of nitrogen to ammonia, but in other cases, e.g., *Rhizobium trifolii*, the reduction occurs when the bacteria are in association with plant roots. Many of these bacterial-plant symbioses are between rhizobial species and legumes and the association is specific. A particular legume species may be nodulated by some rhizobial isolates but not by others. For example, some rhizobial isolates can infect and nodulate soybeans but cannot nodulate garden peas or white clover. The basis of this specificity may involve recognition and binding of the bacterial cell by some component, possibly a lectin, in the plant roots. Thus, fluorescein-labelled soybean binds to 22/25 strains of *Bradyrhizobium japonicum* which infect soybeans but does not bind to any of the 23 strains from 5 rhizobial species that infect other legumes (Bohlool, B. B. and Schmidt, E. L. (1974) Science 185:269-271).

In addition to recognition specificity, there appear to be a variety of specific host-symbiont interactions which occur during nodulation. For example, rhizobial responses effected by the host plant include morphological changes during conversion to the bacteroid state, and the induction of nitrogenase. Plant responses affected by interaction with rhizobial species include nodule development and synthesis of leghemoglobin. Studies of the temporal unfolding of these responses during nodulation suggest that each stage of the process is mediated by a complex series of feedback signals from the host plant to the bacterial symbiont, and from the bacteria to the plant. Many of these signals appear to be specific for each host-symbiont species pair and account for much of the observed host species specificity of most rhizobial strains.

Despite the ability of certain plants to induce nitrogenase activity in a symbiotic relationship with some rhizobial species the genetic analysis of biological nitrogen fixation has previously been confined to free living nitrogen fixing organisms, in particular *Klebsiella pneumoniae*. There are 17 linked nitrogen fixation (nif) genes arranged in at least 7 transcriptional units in the nif cluster of Klebsiella (Kennedy, C. et al. (1981) In *Current Perspectives in Nitrogen Fixation*. (A. H. Gibson, W. E. Newton, eds.) Canberra: Australian Academy of Science, pp. 146-156; and Reidel, G. E. et al. (1979), Proc. Nat. Acad. Sci. U.S.A. 76:2866-2870). Specific designations are assigned to nif genes, e.g. nifH, based on structural homologies to previously identified genes in other nitrogen fixing organisms at the DNA and protein levels. Three of these genes, nifH, nifD and nifK encode the structural proteins of the nitrogenase enzyme complex (viz. the Fe-protein subunit and the $\alpha$- and $\beta$-subunits of the Mo-Fe protein respectively). These genes are linked on the same operon in *K. pneumoniae* and are transcribed from a promoter adjacent to the nifH gene. The remainder of the nitrogen fixation genes contain information required for bacterial attachment, root hair curling, initiation and development of nodules and establishment of symbiotic relationships. In addition, regulatory sequences such as promoters, operators, attenuators, and ribosome binding sites are found adjacent to the coding regions. These regulatory sequences control the expression of the structural genes, i.e., the coding sequences downstream in the 3'-direction of the DNA reading strand.

*Rhizobium trifolii* is an example of a fast-growing rhizobial species with a narrow host range that cannot normally be induced to fix nitrogen in culture. In contrast, a Bradyrhizobium sp. (Parasponia) species has been isolated and this species is a slow-growing organism with a very broad host range capable of an effective symbiotic relationship with a broad variety of tropical legumes as well as the non-legume Parasponia (Ulmaceae) (Trinick, M. J. (1980) J. Appl. Bacteriol. 49:39-53). Bradyrhizobium sp. (Parasponia) can be induced to fix nitrogen in culture although the level of this fixation is about 100-fold less than can be obtained from the free-living *Klebsiella pneumoniae*. Other slow-growing rhizobial species include the commercially significant *Bradyrhizobium japonicum*, which nodulates soybeans.

The genetics of biological nitrogen fixation have been well characterized in the free-living organism *Klebsiella pneumoniae*. The structural genes for nitrogenase (nifH, nifD and nifK encoding the Fe-protein subunit and the $\alpha$ and $\beta$ subunits of the Mo-Fe protein, respectively) have been mapped both genetically and physically (Kennedy, C. et al. (1981) supra. and Reidel, G. E. et al. (1979) Proc. Nat. Acad. Sci. U.S.A. 76:2866-2870). Cloned DNA fragments carrying these sequences have been shown, by Southern blot analysis, to hybridize to homologous sequences in a wide range of nitrogen fixing organisms, including rhizobial organisms (Ruvkun, G. B. and F. M. Ausubel (1980) Proc. Nat. Acad. Sci. U.S.A. 77:191-195).

In spite of the ecological diversity of nitrogen fixing organisms, the physiological structure of the nitrogenase enzyme complex appears to be very conserved. In all cases where the enzyme complex has been purified, two proteins are present. The larger protein (dinitrogenase) contains molybdenum, iron and acid-labile sulfur, and carries the binding site for nitrogen and contains two subunit proteins $\alpha$- and $\beta$-coded by the nifD and nifK genes respectively. The smaller protein (dinitrogenase reductase) contains iron and acid-labile sulfur, and is required for the reduction of the dinitrogenase and for the binding of MgATP used in this reduction. The dinitrogenase reductase is coded by the nifH gene. Chemical and spectral analyses of the purified protein components support a conservation of protein structure between organisms (Scott, K. F. et al. (1981) J. Mol. Appl. Genet. 1:71-81). In some cases the structures are sufficiently similar to allow formation of active hybrid enzymes between purified components, e.g., *Azotobacter vinelandii* and *Klebsiella pneumoniae* (Eady, R. R. and B. E. Smith (1979) In: A Treatise on Dinitrogen fixation I, II, eds. Hardy, R. W., Bottomley, F. and R. C. Burns, New York, Wiley Press pp. 399-490). Not surprisingly, therefore, the region of the nif operon coding for nifH and nifD shows homology at the nucleic acid sequence level with the corresponding sequences in at least 19 other bacterial strains (Ruvkun, G. B. and F. M. Ausubel (1980) Proc. Nat. Acad. Sci. U.S.A. 77:191-195). Although this conservation of structure is generally true, significant differences between nitrogenases from different organisms also exist as can be shown by variable stability following purification and by the fact that active hybrid complexes do not form in all cases (Eady, R. R. and B. E. Smith (1979) supra).

A DNA fragment carrying the Klebsiella pneumoniae nifK, nifD and nifH genes has been isolated from the nif-strain UNF841(Tn5:nifK) and cloned into the Escherichia coli plasmid pBR325. The nucleotide sequences of the nifH gene and of 622 nucleotides of the nifD gene were determined (Scott, K. F. et al. (1981) supra). In addition, the DNA sequence of the nifH gene from Anabaena 7120 has been determined (Mevarech, M., Rice, D. and R. Haselkorn (1980) Proc. Nat. Acad. Sci. U.S.A. 77:6476-6480). A comparison of the two nucleotide sequences demonstrates two interesting features: (1) There is very little homology (31%) between the two sequences although a few stretches (up to 25 bp) are conserved, accounting for the observed interspecies homology of the nifH genes (Ruvkun, G. B. and F. M. Ausubel (1980) supra). (2) In general, the promoter regions show very little sequence homology with the exception of a short region likely to be involved in common functions, e.g., RNA polymerase recognition.

In contrast, a comparison of the amino acid sequences of the dinitrogenase reductase and of the first 207 amino acids of the α-subunit of dinitrogenase of the two species and of another species show a much greater conservatism. The three species used in this comparison are Klebsiella pneumoniae (Kp); Anabaena 7120 (Ab); and Clostridium pasteurianum (Cp) (Tanaka, M. et al. (1977) J. Biol. Chem. 252:7093-7100). The Kp and Cp proteins share 67% amino acid sequence homology, Kp and Ab proteins share 71% homology, and the Cp and Ab proteins share 63%. This amino acid sequence homology is not spread evenly throughout the protein. Some regions are virtually identical—90% to 95% homology), while other regions are only weakly conserved (30-35% homology). The structural conservation appears to be centered around the five cysteine residues common to all three Fe proteins. These cysteine residues are believed to be ligands to the active center.

Comparison of the N-terminal amino acid sequence of the α-subunit of dinitrogenase from Cp and Kp shows very little sequence homology in this region. This is in contrast to the very high conservation of amino acid sequence seen in the amino terminal region of the Fe protein. What little homology exists between Cp and Kp α-subunits is confined to regions around cysteine residues, as in the Fe proteins. These homologous regions are thought to be involved in the catalytic functions of the nitrogenase enzyme complex. Therefore, this structural conservatism is thought not to be the result of recent evolution and dispersal of the nif genes (Postgate, J. R. (1974) Sym. Soc. Gen. Microbiol. 24:263-292) but, rather, is postulated to be related to a conservation of function.

The isolation of some of the genes involved in symbiotic nitrogen fixation in R. trifolii has involved a combination of transposon-induced mutagenesis, rapid screening for in planta specific symbiotic mutants, molecular cloning of the mutant symbiotic gene sequences and subsequent isolation of the corresponding wild type DNA fragment from an R. trifolii gene bank. The presence of a wild type symbiotic gene on the cloned DNA fragment was then confirmed by introducing it into its allelic (symbiotically defective) R. trifolii mutant strain and assaying for the restoration of the symbiotic phenotype (Scott, K. F. et al. (1982) J. Mol. Appl. Genetics 1:315-326). The transposon Tn5 was introduced into R. trifolii by conjugation with E. coli strain 1830. Symbiotically defective mutants were recovered by selecting for kanamycin resistant strains. These transposon induced mutants were screened once on plants to determine which of the colonies carrying the Tn5 insertions were symbiotically defective. The phenotype of recovered mutants varied from the complete loss of ability to nodulate (nod-) to the production of nodules with varying morphology but inability to fix nitrogen (fix5-4). Two nod+ fix− mutants were specifically reported.

DNA isolated from various Tn5-induced symbiotic mutants was digested with EcoRI cleaved pBR322 plasmid DNA. Tn5 contains no EcoRI restriction sites. These recombinant plasmids were transformed into E. coli RRI and the cells carrying Tn5 and flanking R. trifolii sequences were selected by kanamycin resistance encoded on the transposon. The Tn5-containing recombinant plasmid DNA's were isolated, labelled in vitro with $^{32}P$, and used as probes to identify and isolate corresponding wild type sequences. These cloned fragments were also used to examine the extent of symbiotic gene sequence homology in related species. Homologous sequences were found in some of the fast-growing strains tested, but not in the slow-growing B. japonicum. To isolate wild type DNA sequences corresponding to the mutant sequences cloned from different kanamycin-resistant symbiotically defective mutants, several clone banks of DNA fragments from R. trifolii were generated.

To demonstrate the validity of this approach in the isolation of wild type nitrogen fixation symbiotic gene sequences, two presumptive wild types were analyzed for their ability to "correct" the original Tn5-induced lesion in the R. trifolii genome. Two EcoRI fragments of 6kb and 8kb, respectively, carrying the presumptive wild type sequences were first subcloned into the broad host range conjugative plasmid RP4. These recombinant RP4 plasmids were then conjugated from E. coli RRI into the corresponding R. trifolii mutant (i.e., the mutant used to isolate the presumptive wild type) and cells carrying the cloned symbiotic gene were assayed for their ability to carry out a normal nitrogen-fixing symbiosis on clover plants. Assuming that the cloned DNA fragment carried wild type symbiotic gene sequences, it would be expected that the original mutants would be "corrected" by one of two mechanisms. If the cloned DNA carried the complete symbiotic gene, then correction would occur by complementation and every R. trifolii cell carrying the recombinant RP4 would be capable of an effective symbiotic response. However, if the cloned DNA fragment carried only a portion of the symbiotic gene, then correction of the defect could only occur if the mutant sequences in the genome were replaced by those carried on the RP4 plasmid via homologous recombination. In this case, only a few cells, carrying the recombinant RP4, would be capable of an effective symbiotic response. Both types of responses were observed with different cloned strains. The 6 kb isolate appeared to contain a complete symbiotic gene; however, the larger, 8 kb isolate did not contain all of the information necessary to overcome the symbiotic defect of the Tn5-induced mutant clone to which it hybridized.

In general, identification of a bacterial isolate as a rhizobial species has only been previously achieved by demonstration of nodule formation and re-isolation of the same bacterium from the nodules. Furthermore, due to the specificity of the bacterium-host plant interaction, a number of different legume species must be tested. There are a number of characteristics, however, that clearly indicate that a bacterial isolate is a non-rhizobial species (Vincent, J. M., Nutman et al. (1979) in "Identification methods for Microbiologists", F. A. Skinner and D. W. Lovelock, eds. Academic Press, London). Rhizobia are short to medium gram-negative rods so contra-indications include gram positiveness, endospores, large rods or cocci and chain formation. A rapid growth rate in one or two days and the production of color are also indications that the isolate is not a rhizobial species.

Rhizobial isolates can easily be obtained from freshly-collected turgid nodules of a healthy plant. Rhizobial species can also be isolated from soil but in this case, other bacteria are likely to swamp out the rhizobial species on growth media. If rhizobial species are to be isolated from soil, then it is generally desirable to use a legume species as a "trap" host. Again, due to the specificity of the bacterium-host interaction, a number of different legume species must be used or many rhizobial isolates will be lost. It has been stated by an authority on the subject of symbiotic bacteria-plant relationships (J. M. Vincent (1982) in "Nitrogen fixation in legumes" Academic Press, New York, pp. 5-11) that "except under special circumstances (such as when working with an identifiable ("labelled") strain the ability to nodulate a legume remains the final arbiter as to a culture's allocation to the genus Rhizobium and, in some cases, species." Cross-inoculation patterns have been observed among rhizobial species and proposed as a basis for taxonomic groupings. See Lieberman, M. T. et al. (1985), "Numerical Taxonomic Analysis of Cross-inoculation Patterns of Legumes and Rhizobium," Plant Soil 84:225,244.

A number of methods which are suitable for testing nodulation of large and small seeded species have been described (Vincent, J. M. (1970) "A manual for the practical study of root-nodule bacteria" IBP Handbook No. 15, Blackwell Scientific Publications, Oxford). However, if these tests are not meticulously done, the results are unreliable. For example, a slow-growing and a fast-growing species may occur as a mixture and it is quite easy for the cells of the slow-growing form to remain unobserved within a large, gummy colony. In any event, the tests disclosed in the prior art are time-consuming and tedious.

*Rhizobium trifolii* strains specifically infect and nodulate clover plants. These strains contain a number of large plasmids ranging in size from about 180 kilobases (kb) to greater than 500 kb. The plasmids can be separated and it has been shown that nitrogen fixation (nif) genes are located on a particular plasmid. This plasmid is therefore referred to as the Sym (symbiotic) plasmid (Hooykaas, P. J. J. et al. (1981) Nature 291:351). It is apparent that no quick and reliable method exists which allows identification of a specific symbiotic plasmid occurring in a rhizobial species with a limited host range.

In many cloning projects, only one of the two DNA strands is required initially. Many techniques have been used including poly(UG)-CsCl gradients (Szybalski, W. et al. (1971) Methods Enzymol., Grossman, L., and Moldave, K., eds. Vol. 21D Academic Press, New York pp. 383-413), polyacrylamide gels (Maxam, A. and W. Gilbert (1977) Proc. Nat. Acad. Sci. U.S.A. 74:560-564), and exonuclease treatment (Smith, A. J. H. (1979) Nucl. Acids. Res. 6:831-848). An alternative biological approach has been developed using the bacteriophage M13. The replicative form of this phage DNA is a circular double stranded molecule; it can be isolated from infected cells and used to clone DNA fragments after which it can be reintroduced into *Escherichia coli* cells by transfection. M13 phage particles each containing a circular single stranded DNA molecule are extruded from infected cells. Large amounts of single stranded DNA containing a cloned fragment (5-10 μg phage DNA/ml bacterial culture can be easily and quickly recovered (Messing, J. et al. (1977) Proc. Nat. Acad. Sci. U.S.A. 74:3642-3646). The cloning of DNA fragments into the replicative form of M13 has been facilitated by a series of improvements which led initially to the M13mp7 cloning vehicle (Messing, J., Crea, R. and P. H. Seeburg (1981) Nucleic Acids Res. 9:309-321). A fragment of the *E. coli* lac operon (the promoter and N-terminus of the β-galactosidase gene) was inserted into the M13 genome. A small segment of DNA containing a number of restriction cleavage sites was synthesized and inserted into the structural region of the β-galactosidase fragment. The M13mp7 DNA remains infective and the modified lac gene can still encode the synthesis of a functional β-galactosidase α-peptide.

The synthesized DNA fragment contains two sites each for the EcoRI, BamHI, SalI, AccI and HincII restriction enzymes arranged symmetrically around a centrally located PstI site. Therefore, by chance, either strand of a cloned restriction fragment can become part of the viral(+) strand depending on the orientation of the cloned fragment relative to the M13 genome after ligation. Insertion of a DNA fragment into one of these restriction sites can be readily monitored because the α-peptide will be non-functional, so that there will be no β-galactosidase activity.

Following M13mp7, two new single stranded DNA bacteriophage vectors, M13mp8 and M13mp9, have been constructed (Messing, J. and J. Vieria (1982) Gene 19:269-276). The nucleotide sequence of M13mp7 has been modified to contain only one each of the restriction sites (instead of two) and single restriction sites for HindIII, SmaI and XmaI have been added. Thus the restriction sites are EcoRI-SmaI-XmaI-BamHI-SalI-AccI-HincII-PstI-HindIII. These restriction sites have opposite orientations in M13mp8 and M13mp9. DNA fragments whose ends correspond to two of these restriction sites can be "force cloned" to one or the other of these two M13 cloning vehicles which have also been "cut" by the same pair of restriction enzymes. Thus a DNA fragment can be directly oriented by forced cloning. This procedure guarantees that each strand of the cloned fragment will become the (+) strand in one or the other of the clones and will be extruded as single stranded DNA in phage particles.

Restriction endonuclease cleavage fragments with non-complementing ends are seldom joined in a ligation. DNA cleaved by two different restriction endonucleases therefore cannot be circularized or joined to another fragment produced by the same "two different restriction endonucleases" in both orientations. The result is that a recombinant molecule is formed during the ligation reaction with a defined order of the two fragments. Since the orientation of a cloned DNA fragment in the replicative form of M13 vectors determines which of the two DNA strands is going to be the viral strand, the use of M13mp8 or M13mp9 allows the direct preparation of one of the two DNA strands by cloning.

Co-inventors hereof reported the sequence of the *R. trifolii* nifH and nifD genes, as well as the 5' region of the nifH gene in Scott, K. F. et al. (1983), "Biological Nitrogen Fixation: Primary Structure of the *Rhizobium trifolii* Iron Protein Gene," DNA 2:149-155. The possible existence of a repeated sequence from this region was suggested in this article. This article was published less than one year prior to the priority filing dates hereof.

SUMMARY OF THE INVENTION

Figure 1:
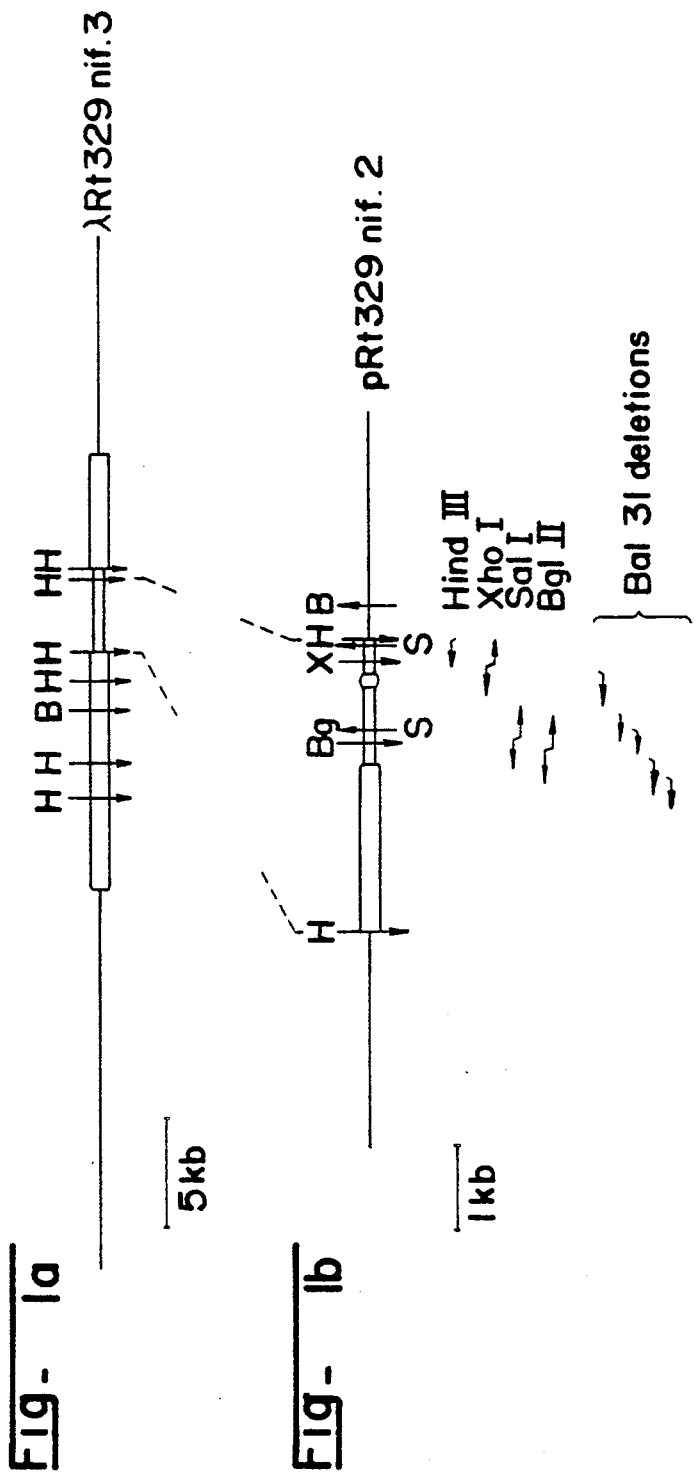
FIG. 1(a) shows a restriction map of *R. trifolii* nifH
FIG. 1(b) shows a restriction map of *R. trifolii* nifD.

This invention provides useful rhizobial promoters for the construction of recombinant molecules to regulate foreign genes for expression under desired conditions. In particular, the promoters act to control expression of the foreign genes within root nodules formed by rhizobial bacterial strains in symbiotic combination with host plants.

A recombinant DNA molecule is provided comprising:

(a) A regulatory region or promoter of a nifH gene of *Rhizobium trifolii*, or derived from or homologous to said nifH gene promoter and capable of activating expression of a nifH gene, preferably a *R. trifolii* nifH gene, in the nodule of a plant, preferably clover; and (b) a foreign structural gene under control of said promoter.

Said promoter isolated from the nifH gene of *Rhizobium trifolii* has a nucleotide sequence as follows:

```
5'   .    .    .   ATT GCT GCT CGA TTG GCG CTT CTA CTC CGC GGC CTC
TTC AGG AGC GAC AGA TGT GAC CAG TTG TCG TCA CCT TTG TCG GCT
TCG TGA CAC GCT TTA GGA TTC TTC GGT CCG GTA TTT TAT CCC TCT
AAG TGT CTG CGG CAG CAC CAA CTT CCG TTC TGC CCC TTC AAT CAG
CTC AAT TGG CAC GAC GCT TGA AAA TTG TTC TCG GGG TGC GAC GGA
ACC ACG CGT CCG ATG TCG CGG CAT CCC CTC GGT CGA TTC GAA CAC
GAA AAG GAA GAA ATA ATG   .   .   .   3'.
```

Functional promoter sequences having at least about 71% homology to the above *R. trifolii* sequence using an incubation temperature of 65° C. are equivalent thereto and are included within the scope of this invention.

Plasmids and bacterial strains, preferably rhizobial strains, comprising said recombinant DNA molecules are also provided. Said molecules may be comprised within the Sym plasmids of rhizobial bacteria or within other plasmids known to the art, or such molecules may be comprised within the chromosomes of the bacterial strains.

Any foreign structural gene known to the art may be used. An example of such a foreign gene is a bacterial toxin gene of *Bacillus thuringiensis*.

Methods are also provided for expressing a foreign structural gene under control of said promoter comprising:

(a) introducing a DNA molecule comprising a foreign structural gene under control of said promoter into a rhizobial strain capable of forming nodules on a plant, preferably clover; and (b) infecting a plant with said rhizobial strain wherein nodules are formed and expression of mRNA or protein coded by said foreign structural gene occurs within said nodules. Plants capable of being infected by particular strains of rhizobia may be readily chosen by those skilled in the art.

Large numbers of bacterial isolates may be recovered from plants or from soil samples. Previously, only expensive and tedious tests were available to definitively identify a specific nitrogen fixing bacterial species or strain capable of a symbiotic interaction with a specific plant species or variety. This invention describes novel compositions and an inexpensive, rapid method for using said compositions to screen bacterial isolates having the ability to nodulate one or more legume species.

DNA fragments are provided comprising an RDS (rhizobial diagnostic segment) derived from a rhizobial strain, generally from the Sym plasmid thereof, exemplified by RDS fragments of *Rhizobium trifolii*. Sequences enabling said molecule to function as a vector, preferably in the form of a plasmid, are also provided.

An RDS (rhizobial diagnostic segment) is found in a rhizobial strain in more than one position. In *Rhizobium trifolii*, an RDS is found on the symbiotic (Sym) plasmid and is located at more than one position on that plasmid. An RDS of a given rhizobial species is a member of a family of substantially homologous (strongly conserved) nucleotide sequences. That is to say, slight sequence variations are observed between RDS sequences located at different sites on the same Sym plasmid or genome. Substantially homologous nucleotide sequences are defined in terms of the conditions which permit hybridization of denatured DNA fragments as described in the Examples hereof, i.e. incubation at 65° C. for 16 hours. Different RDS's which have been obtained from a single strain or different strains of the same species are indeed substantially homologous as measured under the conditions which permit hybridization of fragments as described. Examples of such substantial sequence homology of several RDS's from the symbiotic (Sym) plasmid of a single rhizobial strain are disclosed herein for portions of three such RDS's. RDS's isolated from rhizobial strains of the same species (e.g., *R. trifolii* are substantially homologous with one another, but not with RDS's isolated from rhizobial strains of another species (e.g., *R. meliloti*).

Said RDS may comprise a sequence selected from the group consisting of:

(a) RS-1(a) having a sequence as follows:

```
5'   .    .    .   ATT GCT GCT CGA TTG GCG CTT CTA CTC CGC GGC CTC
TTC AGG AGC GAC AGA TGT GAC CAG TTG TCG TCA CCT TTG TCG GCT
TCG TGA CAC GCT TTA GGA TTC TTC GGT CCG GTA TTT TAT CCC TCT
```

```
         AAG TGT CTG CGG CAG CAC CAA CTT CCG TTC TGC CCC TTC AAT CAG
         CTC AAT TGG CAC CAC GCT TGA AAA TTG TTC TCG GGG TGC GAC GGA
         ACC ACG CGT CCG ATG TCG CGG CAT CCC CTC GGT CGA TTC GAA CAC
         GAA AAG GAA GAA ATA ATG GCT GCT CTG CGT CAG ATC GCG TTT TAC
         GGA AAG GGA GGC ATT GGC AAA TCC ACT ACA TCC CAG AAT ACG CTC
         GCT GCC CTC GTC GAA CTT GGG CAG AAA ATC CTC ATC GTC GGC TGC
         GAC CCA AAA GCT GAT TCG ACG CGA TTG ATC CTG AAC TCC AAA GCG
         CAG GGC ACG GTT CTG GAT CTA GCC GCA ACG AAG GGT TCA GTT GAA
         GAT CTG GAA CTC .  .  .  .  3';
```

(b) sequences hybridizable thereto, preferably over at least about 100 base pairs under incubation conditions of about 65° C.;

(c) RS-1(b) having a sequence as follows:

```
5'  .   .   .   AT C GAT GCG CGG CTC ATT CGA CCG AGA GTT GTA GCG
         CAT TGA AGC CGA CCC ACT GCT TTC TCT TCA GGA GCA ACA TGA CAT
         GTG TCC GAC ATT GTC GTT TCC TTT GTC GAC TTC GAG ACA CGT CTT
         AGG ATT CTT CGG TCC GAT ATT TTA TCC CTC TAA GTG TTT GCG GCA
         CAC CAA ATT CCG TTC TGC CAC ATC AAT CCG CCC AGT CTG GCA CGA
         CGC TTG AAA ATT GTT CTC GGG CTG CGA CGG AAC CAG CCG CGT CCG
         ATG TCG CGG CAT CAC CTC GGT CGG TTC GAA CAC GAA AAG GAA GCA
         ATA ATG GCT GCT CTG CGT CAG ATC GCG TTT TAC GGA AAG GGA GGC
         ATT GGC AAA TCC ACT ACA TCC CAA AAT ACG CTC GCT GCC CTT GTC
         GAA CTT GGG CAG AAA ATC CTC ATC GTC GGC TGC GAC CCA AAG GCT
         GAT TCG ACG CGA TTG ATT CTG AAC TCC AAA GCG CAG GGC ACT GTT
         CTG GAT CTA GCC GCA ACG AAG GGT TCA GTC GAA GAT CTG GAA CTC
         .  .  .  3';
```

(d) sequences hybridizable thereto, preferably over at least about 100 base pairs under incubation conditions of about 65° C.;

(e) RS-2 having a sequence as follows:

```
5'  ...         CTG CAG AAA GTT AAC AAA ACA TGA GAC TGA AGA TGC
 TCA AGG GAT AAT CGC GCG CTT CGA AAA TGT TTG CGA CAG GCC CCT
 CTG CTG TCT CTT CAG GAT ACT CAC GAC ATG TGT GCG ACA TTG TCG
 TCA ACT TTG TCG ACT TCG TGA CAC GTC TTA GGA TTC TTC GGT CCG
 GTA TTT TAT CCC TCT AAG TGT TTG CGG CAG CGC CAA ATT CCG TTC
 TGC CAC ATC AAT CCG CCC AGT CTG GCA CGA CGC TTG AAA ATT GTT
 CTC GGG CCG CGA CGG AAC CAC GCG GCC GAG TCG CGG CAT CAC CTC
 GGT CGG TTC GAA CAC GAA AAG GAA GCA ATA ...  3'
```

(f) sequences hybridizable thereto, preferably over at least about 100 base pairs under incubation conditions of about 65° C.;

(g) RS-3 having a sequence as follows:

```
5'  ..          GAT CGA CCG AGA GGT GCG TCA TTG GGG CTC GCC CTC
 TGC GGC TTC TTC AGG GGC ACC ATG ACA TAT GTG CGA CAT TGT CGT
 CGC TTT GTC GGC TTC GTG ACA CGG TTT AGG ATT CTT CGG TCC AGT
 ATT TTA AAC CTC TAA GTG TCT GTG GCA GCA CCA ACT TTC GTT CTG
 CCT ATC AAT CAG CTC AAT TGG CAC GAC GCT TGA AAA TTG TTC ACG
 GGC TGC GAC GGA GCC GGC TTG TAT GAA ACG GAG ATC AGC ATG TCC
 ATC CGA AAA AGA AAG TTC TT ...  3'
```

(h) sequences hybridizable thereto, preferably over at least about 100 base pairs under incubation conditions of about 65° C.

A process is also provided for determining whether an unknown rhizobial isolate does or does not belong to a given rhizobial species comprising the steps of:

(a) purifying DNA of the isolate by means known to the art;

(b) cleaving the DNA of the isolate with a restriction endonuclease as known to the art to generate isolate DNA restriction fragments of various sizes;

(c) fractionating the isolated DNA restriction fragments on the basis of molecular size as known to the art on a supporting substance, preferably on a nitrocellulose filter as described by Southern, E. M. (1975) J. Molec. Biol. 98:503–517;

(d) incubating the isolate DNA restriction fragment fractions with a labelled DNA probe comprising an RDS of the given rhizobial species, under hybridization conditions, preferably using incubation at about 65° C., such that substantially homologous segments, preferably of at least about 100 nucleotides length, will hybridize to one another;

(e) determining whether one or more DNA restriction fragments hybridize with the RDS probe;

(f) determining that the species of the rhizobial isolate coincides with the given rhizobial species if the RDS probe hybridizes with more than one isolate DNA restriction fragment, and if not that the isolate species does not coincide with the given rhizobial species.

The RDS probe used in said process preferably comprises at least about 100 nucleotides of a sequence selected from the group consisting of RS-1(a), RS-1(b), RS-2 and RS-3 of *Rhizobium trifolii*.

A process is also provided for determining whether an unknown rhizobial isolate does or does not belong to a given rhizobial strain. Within a given species having homologous RDS's, the strains may be distinguished by means of characteristic patterns formed by the hybridizing fragments because of restriction fragment length polymorphisms (RFLP's). RFLP techniques are known to the art. The method for using RDS's to distinguish rhizobial strains comprises the steps of:

(a) purifying DNA of the isolate;

(b) cleaving the DNA of the isolate with a restriction endonuclease to generate isolate DNA restriction fragments of various sizes;

(c) fractionating the isolated DNA restriction fragments on a supporting substance on the basis of molecular size whereby each fragment has a particular placement on said supporting substance correlated with its size;

(d) incubating the isolate DNA restriction fragment fractions on said supporting substance with a labelled DNA probe comprising an RDS of the given rhizobial strain, under hybridization conditions, preferably using incubation at about 65° C., such that substantially homologous segments, preferably of at least about 100 nucleotides length will hybridize to one another;

(e) identifying the number of and placement isolate DNA restriction fragments on said supporting substance that hybridize with the RDS probe;

(f) determining that the strain of the rhizobial isolate coincides with the given rhizobial strain if the RDS probe hybridizes with more than one isolate DNA restriction fragment in the placement pattern on said supporting substance characteristic of said given strain, and if not that the isolate strain does not coincide with the given rhizobial strain.

The RDS probe used in said process preferably comprises a total or partial sequence of RS-1(a), RS-1(b), RS- and RS-3 of *Rhizobium trifolii.*

For the sake of convenience and clarity, the following definitions are presented below:

(a) Promoter: the nucleotide sequence upstream from the transcriptional start site containing all the regulatory regions required for transcription.

(b) Regulatory region: DNA sequence(s) necessary but not necessarily sufficient to turn on expression of a gene. A gene is "under control of" a regulatory region when said sequences operate to determine whether the gene is active or inactive.

Translational start site: the ATG codon translated into a methionine residue at the amino terminus of an open reading frame.

(d) Transcription start site: the first deoxynucleotide to be transcribed into an RNA sequence of an mRNA sequence.

(e) Foreign gene(s): (a) structural gene(s) isolated from an extraneous source organism.

(f) Vector: a means, such as a plasmid, for transferring genetic material into a host organism with a single replication origin which carries and replicates one or more fragments of foreign DNA.

(g) Foreign DNA: a fragment of DNA isolated from an extraneous source organism, i.e. an organism other than the host organism.

(h) Homology: identity of nucleotide sequences. "Percent homology" refers to the number of identical nucleotide sequences in a given number of overlapping base pairs. A "base pair overlap" is simply a specified number of contiguous base pairs of two different sequences lined up together so that each base pair of one sequence can be checked for identity with the corresponding base pair of the other sequence. When no number of overlapping base pairs is given, the total number of base pairs in the sequence to which the "homologous" sequence is being compared is to be understood.

(i) Transforming: refers to the transfer of foreign DNA to a host organism so as to enable expression of the foreign DNA in the host organism. A "transformed" organism is one which is distinguishable from a naturally-occurring organism because of the presence of the foreign DNA.

(j) Recombinant DNA molecule: A DNA molecule prepared by human intervention. It may be a piece of a larger DNA molecule such as a plasmid or a genome, or it may comprise several such pieces ligated together. A composite gene, which comprises a structural gene in combination with a promoter with which it is not found in nature, is an example of a recombinant DNA molecule.

DETAILED DESCRIPTION OF THE PREFERRED EMBODIMENTS

Table 1 shows the sequence of the *R. trifolii* nifH genes, 276 bp preceding the gene and the N-terminal 141 codons of nifD following nifH.

Table 2 shows partial sequences of RDS fragments RS-1(a), RS-1(b), RS-2 and RS-3.

Table 3 shows extended sequences of RDS fragments RS-1(a), RS-1(b), RS-2 and RS-3.

Table 4 shows amino acid expression sequences for RDS fragments RS-1(a), RS-1(b), RS-2 and RS-3.

Table 5 describes rhizobial strains tested using the process of this convention.

A recombinant plasmid is disclosed, wherein there is a wide host range vector containing an inserted fragment of DNA including a nif regulatory region of a nitrogenase complex gene of a rhizobial species and a foreign structural gene under the control of the regulatory region. Since the regulatory region and the foreign genes are carried on plasmids which can be lost from naturally-occurring rhizobial species, a method for transferring these genes from a vector to the bacterial chromosome is also described. Novel rhizobial strains are thereby generated, having a chromosomally integrated composite gene including a nif gene regulatory region and a foreign gene. Also disclosed are novel rhizobial strains wherein one or more nitrogenase genes of the same or different rhizobial species is integrated into the chromosome.

The invention is based in part on the isolation and characterization of the regulatory regions controlling the nitrogen fixation (nifH) genes of *Rhizobium trifolii* strains. A regulatory region can be combined with a structural gene isolated from an extraneous source organism ("foreign gene" herein) and combined in a plasmid to provide a novel plasmid bearing the foreign gene expressible under control of the nifH gene regulatory region, and to provide a novel microorganism transformed by the novel plasmid. Alternatively, the composite gene, including the foreign structural gene and nifH gene regulatory region, can be integrated with the chromosome of a host bacterial strain in order to maximize the stability of the trait conferred by the composite gene. Furthermore, a novel rhizobial strain can be constructed in which a nifH regulatory region together with the structural gene or genes it normally controls is integrated with the host chromosome to enhance stability of the ability to fix nitrogen.

The novel plasmids disclosed herein are useful for amplifying the quantities of composite genes, for transferring such genes to selected bacterial hosts, for generating new host bacterial strains and as intermediates for the construction of other plasmids having one or more of the foregoing uses. The bacterial strains of the present invention are useful for expressing the composite gene, under certain conditions, to provide a useful product, to confer an advantageous property to a plant or to improve the rate, quality or efficiency of the nitrogen fixation process. In particular, the properties of the novel strains are manifested within root nodules formed by novel rhizobial strains of the invention in symbiotic combination with a host plant. Depending upon the gene chosen for expression in the nodule, the nodule then serves as a production source for a protein coded by the gene.

Examples of proteins which can be expressed in root nodules include the insect-toxic protein of *Bacillus thurinoiensis* (Wong, H. C. et al. (1983) J. Biol. Chem. 258:1960), the hydrogenase found in some but not all rhizobial strains (Cantrell et al. (1983) Proc. Nat. Acad. Sci. USA 80:181), metallothionein (Karin, M. and Richards, R. I. (1982) Nucl. Acids Res. 10:3835) and prolactin (Cooke, N. et al. (1981) J. Biol. Chem. 256:4007–4016). The foregoing list is not intended as limiting, but merely as exemplary of the broad range of possibilities for synthesis of proteins in root and stem nodules of plants. In general the invention makes it possible to produce any protein that may be of use, either as a product extracted from the nodule, as an excretion product of the nodule, conferring an advantage for the host plant, or as a functional protein within the nodule itself, improving the effectiveness of the symbiotic interaction. In addition to the proteins disclosed herein, others will be apparent to those of ordinary skill in the art, taking advantage of the known or subsequently discovered properties of root nodules and of specific proteins.

A major advantage conferred by gene expression under control of a nifH regulatory region in root nodules is derived from the inventors' recognition that such expression is regulated in a similar manner as the expression of the nifH genes themselves. The foreign gene is only minimally expressed, if at all, in the free-living bacteria. However, the gene is maximally expressed within the root nodule. Furthermore, because of the specific nature of the host-bacterium symbiosis, gene expression occurs only in the selected plant species recognized by the modified bacterial strain. These properties consequently ensure, first, that the foreign gene expression provides maximum local effect of the expression product, and second, that environmental side effects are limited since gene expression can be confined to the nodular tissue of the selected crop or plant variety.

Despite the fact that many structural genes of the rhizobial nif regions hybridize with previously isolated nif gene segments, as described, supra some rhizobial nif regions do not hybridize, as shown by Scott et al., supra. Furthermore, the regulatory regions so far identified are substantially different from one another. In fact, as discovered in the course of the experiments leading to the present invention, the organization of the nifH, D and K genes differs within the rhizobial species in a manner difficult to generalize at present. Many species have a single regulatory region apparently controlling the H, D and K genes. However, as disclosed herein, the Bradyrhizobium sp. (Parasponia) has a separate, distinctive region regulating expression of nifH and this gene maps at a different genetic locus from nifD or K. As a consequence of the results herein disclosed, it now appears that the regulatory regions (promoters) of the nif genes of rhizobial species are individually distinctive and variable in number and genetic locus from strain to strain. The techniques disclosed herein provide the first systematic means for isolating and genetically manipulating such regulatory regions for useful purposes.

Cloned DNA fragments of the nifH, nifD and nifK genes of the free living organism *Klebsiella pneumoniae* were used to identify and isolate the corresponding symbiotic genes of *Rhizobium trifolii*. These three genes (nifH, nifD and nifK) constitute the nitrogenase complex. They may all be closely linked or they may be unlinked. In particular, a recombinant plasmid (pKnif-2) carrying *K. pneumoniae* DNA and coding for the entire nifH gene and the N-terminal 207 amino acids of nifD gene has been cloned and used as a hybridization probe. (Scott, K. F., Rolfe, B. G. and J. Shine (1981) J. Mol. Appl. Genet. 1:71–81).

To isolate the nitrogenase complex structural genes from *R. trifolii* a gene bank of *R. trifolii* ANU329 DNA was constructed by partial cleavage of genomic DNA with Sau3A and ligation into BamHI-cleaved DNA isolated from the phage vector lambda-Charon 28 (Scott, K. F. et al. (1982) J. Mol. Appl. Genet. 1:315–326). This gene bank was screened by hybridization with $^{32}$P-labelled pKnif-2 sequences. A number of positively-hybridizing clones were isolated and restriction maps were constructed. A restriction endonuclease map of the *R. trifolii* nifH as determined from recombinant plasmid pRt329nif-3 is shown in FIG. 1a. Shaded areas indicate regions of pKnif-2 homology. Restriction sites are abbreviated as follows: B=BamHI; Bg=BglII; H=HindIII; S=SalI; and X=XhoI. The positively-hybridizing clones were subcloned into the plasmid vector pBR322. A vector as defined herein includes a plasmid with a single replication origin which carries and replicates one or more fragments of foreign DNA. The recombinant plasmids were transformed into *E. coli* HB101. The resulting recombinant plasmids were extensively mapped by restriction endonuclease analysis and were the source of DNA used for direct sequence analysis.

Sequence analysis was carried out by the chemical method (Maxam, A. M. and W. Gilbert (1980) Methods in Enzymology 65:499–560) from defined restriction sites and by a method based on the generation of a series of deletions with the double stranded exonuclease Bal31 (Legerski, R. J., Hodnett, J. L. and H. B. Gray (1978) Nucleic Acids Res. 5:1445–1464) followed by subsequent cloning of these deleted fragments into the phage vector M13mp9 (Vieira, J. and J. Messing (1982) Gene 19:259–268) and sequence analysis by the chain termination method (Sanger, F., Nicklen, S. and Coulson, A. R. (1977) Proc. Nat. Acad. Sci. U.S.A. 74:5463–5467). To illustrate the procedures, a series of overlapping M13 clones of known orientation from recombinant plasmid pRt329nif-2 was constructed (FIG. 1b) enabling the rapid sequence analysis of some 1500 base pairs (bp) of nitrogenase complex-specific *R. trifolii* DNA. The shaded region indicates the location of the nifH and nifD gene sequences. Restriction sites are abbreviated as for FIG. 1a (see supra). The DNA sequence of the *R. trifolii* SU329 nifH gene, 276 bp preceding the gene and the N-terminal 141 codons of nifD following nifH is shown in Table 1. The nifH coding region was assigned to an open reading frame of 297 codons based on the homology of this translation product with previously determined Fe-protein sequences (Scott, K. F. et al. (1981) J. Mol. Appl. Genet. 1:71–81). The open reading frame is preceded by the sequence (5'-AGGA-3') analogous to the ribosome binding site sequence found in *E. coli* (Shine, J. and L. Dalgarno (1975) Nature 254:34-38). The same sequence precedes an open reading frame following nifH. This reading frame has been assigned as the *R. trifolii* nifD gene also on the basis of sequence homology of its predicted translation product to the partial amino acid sequence analysis of the Mo-Fe protein subunit α from *Clostridium pasteurianum* (Hase, T. et al. (1981) J. Biochem. 90:295-298) and the predicted amino acid sequence encoded by the 5'-portion of the *K. pneumoniae* nifD gene (Scott, K. F. et al. (1981) J. Mol. Appl. Genet. 1:71-81). The sequence data show clearly that the nifH and nifD genes are linked on the same operon in *R. trifolii* as is the case in *K. pneumoniae*, *R. meliloti* (Ruvkun, G. B. et al. (1982) Cell 29:551-559) and in *B. japonicum* strain 110 (Hennecke, H. (1981) Nature 291:354-355). This is in contrast to the organization of the nifH and nifD genes seen in the non-legume symbiont Bradyrhizobium sp. (Parasponia ANU289 (see infra). The DNA sequence of *R. trifolii* 5' to the nifH gene (i.e., the fragment of DNA controlling expression of nifH structural genes, Table 1) shares very little homology to the corresponding sequences of other rhizobial species (Torok I. and A. Kondorosi (1981) Nucleic Acids Res. 9:5711-5723) or Bradyrhizobium sp. (Parasponia) ANU289 (see infra). The sequence of the *R. trifolii* Fe-protein can be predicted from the DNA sequence of the nifH gene (Table 1). The amino acid sequence is strongly conserved when compared to *C. pasteurianum* (65% homology) and to *K. pneumoniae*, Anabaena 7120 and *Azotobacter vinelandii* (70% homology). The homology between the amino acid sequences of *R. trifolii* and the closely related legume symbiont *R. meliloti* is even greater, i.e., 90%.

TABLE 1

Sequence of the *R. trifolii* nifH genes, 276bp preceding the gene and the N-terminal 141 codons of nifD following nifH.

```
  1 ATTGCTGCTCGATTGGCGCTTCTACTCCGCGGCCTCTTCAGGAGGCGACAGATGTGACCAGTTGTCGTCACCTTTGTCGGCTTCGTCACACGCTTTAGGAT  100

101 TCTTCGGTCCGGTATTTTATCCCTCAAGTGTCTGCGGCAGCACCAACTTCCGTTCTGCCCCTTCAATCAGCTGAAAGGAAGAAATAATGGCTGCTCTGCGTCAGATCGCG  200

201 CTCGGGCTGCGACGGAACCACGCGTCCGATGTCGCGGCATCCCTCGGTTGCGAGGGCATCCCTCGATTCGAACGAAAAGGAAGAAATAATGGCTGCTCTGCGTCAGATCGCG
                                                                                                              Met Ala Ala Leu Arg Gln Ile Ala  300

301 TTTTACGGAAAGGAGGCATTGGCAAATCCACAACATCCCAGAATACGCTCCGCTGCCCTGGTCGAACTTGGGCAGAAAATCCTCATCGTCGGCTGCGACC
     Phe Tyr Gly Lys Gly Gly Ile Gly Lys Ser Thr Thr Ser Gln Asn Thr Leu Ala Ala Leu Val Glu Leu Gly Gln Lys Lys Ile Leu Ile Val Gly Cys Asp P  400

401 CAAAGCTGATTGACGGCGATTCGAACTTCCAAAGGCCAGGGCACGGTTCTGGATCGGGCAGCACCGGCACCGGTCTCCAAAGCTTCAGTTGAAGATCTGGAACTCGG
    ro Lys Ala Glu Thr Arg Leu Ile Leu Asn Ser Lys Ala Gln Gly Thr Val Leu Asp Ser Leu Ala Ala Thr Lys Gly Ser Val Glu Asp Leu Glu Leu Gl  500

501 CGATGTGCTCAAAACTGGCTACGGCGCATCAAATGTGTGAGTCGGGCGCCCTGAACCCGGCTGCCGGATCGGCCCTGAACCGGCGCCGCGTCATAACGTCGATC
    y Asp Val Leu Lys Thr Gly Tyr Gly Gly Ile Lys Cys Val Glu Ser Gly Gly Pro Glu Pro Gly Val Gly Cys Ala Gly Arg Gly Val Ile Thr Ser Ile  600

601 AACTTCTTGGAAGAAAACGGCGCCTACGACGATGTCGACTACGTCTCCTATGACGTGCTCGGAGACGTGGTGTGCGGGGCTTTGCTATGCCAATCCGCG
    Asn Phe Leu Glu Glu Asn Gly Ala Tyr Asp Asp Val Asp Tyr Val Ser Tyr Asp Val Leu Gly Asp Val Val Cys Gly Gly Phe Ala Met Pro Ile Arg G  700

701 AGAACAAGGCTCAGGAAATCTACATCGTCGGTGAGATGATGGCTCTGTATGCTGCAAACAACATCGCGAGGGCATCCTCAAATATGCCAGCGC
    lu Asn Lys Ala Gln Glu Ile Tyr Ile Val Met Ser Gly Glu Met Met Ala Leu Tyr Ala Ala Asn Asn Ile Ala Arg Gly Ile Leu Lys Tyr Ala Ser Al  800

801 CGGAAGCGTGCGGCCTGATTTGTAATGAGCGGCAGACCGAGCTTAGAAGCGGCAGGTGAAGCCTCGCTGAAGCGCTGAAGCGCTCAATTCAAAGCTC
    a Gly Ser Val Arg Leu Gly Leu Ile Cys Asn Glu Arg Gln Thr Arg Glu Leu Asp Arg Ala Glu Ala Leu Ala Ala Lys Leu Asn Ser Lys Leu  900

901 ATTCACTTCGTGCCGCGAGACAACATCGTCCAGCACGCGGAGCTTAGAAAGATGACCGTGATCCAATACGCCGTCCAAACAGCGCCGGAATATC
    Ile His Phe Val Pro Arg Asp Asn Ile Val Gln His Ala Glu Leu Arg Lys Met ThreVal Ile Gln Tyr Ala Val Pro Arg Ser Lys Gln Ala Ala Glu Tyr A  1000

1001 GATGGCTGGCCGAGAAGATCCAATTCGGGAAGGCACTACTCCTATCCTATGGAGGAGCTGGAGGACATGCTACTGACTTCGGAAT
     rg Trp Leu Ala Glu Gly Lys Ile His Ser Asn Ser Gly Lys Gly Thr Ile Pro Thr Pro Ile Thr Met Glu Glu Leu Glu Asp Met Leu Asp Phe Ile I  1100

1101 CATGAAGTCGACGAGCAGATGCTTGAAGAACTTCTCGCCAAAGAGGTCAGGCGCCATAACAGTCCCGCCATAGAGCGGAGCGGAATGA
     e Met Lys Ser Asp Glu Gln Met Leu Glu Leu Leu Ala Lys Glu Val Gln Ala Ala Val Ala Pro End  1200

1101 CATGAAGTCGACGAGCAGATGCTTGAAGAACTTCTCGCCAAAGAGGTCAGGCGCCATAACAGTCCCGCCATAGAGCGGAGCGGAATGA  1200
```

TABLE 1-continued

Sequence of the *R. trifolii* nifH genes, 276bp preceding the gene and the N-terminal 141 codons of nifD following nifH.

```
1201 CGCACCGGTCAATCGACAAACCATGCCTCCTTGTCGAGGCTCCATGCGAACCTTCGAGAGAGGAAAGGCCCTATGAGCCTCGACTACGAGAACGACGGT   1300
                                                                         Met Ser Leu Asp Tyr Glu Asn Asp Gly
1301 GATTTGCACGCAAGGCTTATAGACGAGGTACTCTCGCAGTATCCGGATAAGACGGCTAAGCGCCGCAAAAAGCACCTTGGCGTCGCGAAGGGCAGAGAGG   1400
     Asp Leu His Ala Arg Leu Ile Asp Glu Val Leu Ser Gln Tyr Pro Asp Lys Thr Ala Lys Arg Arg Lys His Leu Gly Val Ala Lys Gly Arg Glu A
1401 CACTCGAGCAGGGCTCCGATGCGCTTTGCGAGACTGGGGTGAAATCCAACATCAAGTCTATTCCGGGCGTGATGACCGTCGGGCTGCGCTTACGCCGG   1500
     la Leu Glu Gln Gly Ser Asp Ala Leu Cys Glu Thr Gly Val Lys Ser Asn Ile Lys Ser Ile Pro Gly Val Met Thr Val Arg Gly Cys Ala Tyr Ala Gl
1501 CTCGAAGGGGTCGTGTGGGGCCCGATCAAGGATATGGTCCATATCTCGCATGGCCCTGTCGGTTGTGGGCACTATTCTTGGTCGCAACGCCGCAACTAT   1600
     y Ser Lys Gly Val Val Trp Gly Pro Ile Lys Asp Met Val His Ile Ser His Gly Pro Val Gly Cys Gly His Tyr Ser Trp Ser Gln Arg Arg Asn Tyr
1601 TACGTCGGTCTGACGGGTGTCGACGCCTTTGTCACCATGCAATTCACGTCTGACTTTCAAGAAAAGGATATTGTTTTTGGTGGCGACAAAAAGCTT     1696
     Tyr Val Gly Leu Thr Gly Val Asp Ala Phe Val Thr Met Gln Phe Thr Ser Asp Phe Gln Glu Lys Asp Ile Val Phe Gly Gly Asp Lys Lys Leu
```

A principal feature of the present invention is the construction of a plasmid having an inserted foreign structural gene under control of a nitrogenase complex promoter. The structural gene must be inserted in correct position and orientation with respect to the nitrogenase complex promoter in order to obtain expression of the structural gene controlled by the promoter. Position has two aspects. The first relates to on which side of the promoter the structural gene is inserted. It is known that the majority of promoters control initiation of transcription and translation in one direction only along the DNA. The region of DNA lying under promoter control is said to lie "downstream" or alternatively on the 3'-side of the promoter. Therefore, to be controlled by the promoter, the correct position of structural gene insertion must be "downstream" from the promoter. The second aspect of position refers to the distance, in base pairs, between functional elements of the promoter, for example the transcription initiation site, and the translational start site of the structural gene. Substantial variation appears to exist with regard to this distance, from promoter to promoter. Therefore, the structural requirements in this regard are best described in functional terms. Optimum spacing can be achieved by experiments varying the length of this distance. As a first approximation, reasonable operability can be obtained when the distance between the promoter and the inserted structural gene is similar to the distance between the promoter and the gene it normally controls. Orientation refers to the directionality of the structural gene. By convention, that portion of a structural gene which ultimately codes for the amino terminus of a protein is termed the 5' end of the structural gene, while that end which codes for amino acids near the carboxyl end of a protein is termed the 3' end of the structural gene. Correct orientation of a structural gene is with the 5' end thereof proximal to the promoter. An additional requirement in the case of constructions leading to fusion protein expression is that the insertion of the structural gene into an existing nitrogenase complex structural gene sequence must be such that the coding sequences of the two genes are in the same reading frame phase, a structural requirement which is well understood in the art.

In order to express foreign genes on the 3'-side of the nitrogenase complex regulatory sequence, it is first advantageous to construct a double stranded DNA sequence corresponding to the nifH regulatory sequence. To achieve this, synthetic DNA primer complementary to the ribosome binding site of the mRNA and extending a few nucleotides to the side thereof is first constructed. Then the cloned nifH fragment is excised from the vector, purified and the excised nifH fragment is ligated into appropriate M13 vectors. The resultant recombinant DNA plasmids are then transformed into E. coli strains, and single colonies are propagated. Those colonies which extrude single stranded templates corresponding to the mRNA strand are isolated. The synthetic DNA is used as a primer on these single stranded templates to generate double stranded DNA by primer extension with DNA polymerase I (Klenow fragment). This double stranded DNA will extend from the ribosome binding site to a indeterminate point within the M13 vector. Any single stranded regions are removed by S1 nuclease treatment.

Then synthetic EcoRI linkers are ligated to the DNA fragments followed by digestion with EcoRI and that restriction endonuclease (termed endonuclease A for generality) which recognizes the restriction site at the 5' end of the nifH. The resultant DNA fragments are then cloned into an EcoRI-endonuclease A cleaved plasmid, transformed into a suitable E. coli host and amplified. The choice of plasmid is based on principles of operating convenience and location of the appropriate restriction sites, as will be understood by those of ordinary skill in the art.

Following amplification, isolation and repurification, this same plasmid is then cleaved with endonuclease A and treated with S;-nuclease or BAL-31 for a short time to produce blunt ended fragments. The plasmid is now cleaved with EcoRI and the fragment is cloned into the wide host range plasmid pRK290 which has been cleaved with SmaI-EcoRI (pRK290-nif regulatory fragment construct). Alternatively, another wide host range plasmid, pSUP204, can be used to construct the recombinant nifH regulatory plasmid. Alternatively, the DNA fragments provided with EcoRI-endonuclease A-specific ends are initially cloned into a mobilizable broad host range vector capable of replication in either E. coli or most other gram-negative bacteria, such as pSUP104 or pSUP204, described by Puhler, A. et al. supra. After amplification, the recombinant plasmid is transferred directly to the desired recipient strain.

In order to clone and express foreign genes, appropriate DNA fragments carrying these foreign genes are isolated and synthetic EcoRI linkers are ligated to the fragments (EcoRI-foreign gene-EcoRI). These EcoRI-foreign gene-EcoRI DNA fragments are then ligated into EcoRI-cleaved vector DNA, for example, pSUP104 or pSUP204, resulting in a nif-regulated expression plasmid, pSS104 or pSS204, respectively, and transformed into E. coli. After selection and amplification, the nif expression plasmid is then transferred with the aid of helper plasmids to the appropriate rhizobial or Acrobacterium strain by mating.

The transformed rhizobial strains are then used to infect appropriate legumes which are subsequently assayed for the production of foreign mRNA and/or protein.

The nif and nod genes of R. trifolii which have been cloned and analyzed are all carried on the same large symbiotic (Sym) plasmid. However, plasmids are lost rather easily from bacterial strains, leading to the loss of expression of those genes carried on the plasmids. One method o stabilizing the expression of certain genes carried on plasmids, or, for that matter, any foreign DNA segment, would be the introduction of such genes or foreign DNA segments, hereinafter termed "introduced DNA", into the chromosome of the host bacteria. Such a system employs a "suicide vector" and, preferably, a transposon.

Suicide vectors are plasmid molecules which replicate stably in one bacterial host (in this case E. coli, but fail to replicate in a different bacterial species (e.g., Rhizobium trifolii. Transposons are genetic elements which are able to move (translocate) from one location to another in DNA. The translocation process is mediated by gene products encoded on the transposon and is dependent upon the integrity of repeated sequences (directly or indirectly repeated) located at each end of the transposon. Transposons generally carry a gene (or genes) encoding resistance to one or more antibiotics. The transposon and the suicide vector are linearized and relegated into a single recombinant DNA molecule.

The general method of transferring introduced DNA segments to the chromosome of a gram-negative bacterial strain other than *E. coli* is outlined here. The introduced DNA fragments to be introduced can be generated in a number of ways: (a) by restriction with site specific restriction endonucleases, (b) by partial or complete digestion with restriction endonucleases which generate DNA fragments having blunt ends, (c) by digestion of DNA with the enzyme DNAseI in the presence of $Mn^{2+}$ ions thus generating random fragments which are generally blunt-ended, or (d) by shearing the DNA into large fragments.

In the preferred method, the suicide vector carrying a transposon with an antibiotic resistance gene is linearized and the appropriate fragment of introduced DNA is ligated into a "co-integrated recombinant molecule." The fragment of DNA is inserted into a restriction endonuclease site within the transposon such that the insertion does not disrupt normal transposition nor expression of the drug resistance marker. This ligated DNA is then transformed into an *E. coli* strain in which it can be amplified and mobilized for transfer into other gram-negative bacteria.

Introduction of the cloned introduced DNA fragment from this *E. coli* strain into the chromosome of any gram-negative bacterium, e.g., *R. trifolii* is most conveniently achieved by the process of bacterial conjugation. The *E. coli* strain carrying the suicide vector which contains an antibiotic resistance gene, is mixed with cells of the antibiotic sensitive gram-negative strain on the surface of a nutrient agar plate. The plate is incubated for a period (4-16 hr.) at the optimum temperature of the gram-negative strain and during this time, cells of each bacterial species come into physical contact (conjugation) and the suicide vector is transferred from the donor *E. coli* to the recipient gram-negative strain. The cell mixture is washed off the plate and spread on an agar plate which is selective for the antibiotic resistance. It is preferred to include selection means that select against growth of the *E. coli* parent strain once the conjugation is completed.

Since the suicide vector containing the introduced fragment of DNA cannot be amplified autonomously in the recipient gram-negative strain, a transfer of genetic material to the bacterial chromosome can occur in one of three ways: (a) If a fragment of the recipient gram-negative bacterial chromosome (BC) has been previously inserted into the suicide vector (SV) thus creating a region of homology between the suicide vector and the recipient gram-negative bacterial chromosome, then a single reciprocal recombination will result in the incorporation of the entire "co-integrated recombinant molecule" into the chromosome of the recipient gram-negative bacterial chromosome. (b) If a fragment of the recipient gram-negative bacterial chromosome has been previously inserted into the suicide vector thus creating a region of homology between the suicide vector and the recipient gram-negative bacterial chromosome and then an introduced DNA fragment and a drug resistance gene are inserted into this region of homology, a double reciprocal recombination event will incorporate only the introduced DNA fragment and the drug resistance gene into the chromosome of the recipient gram-negative bacterial strain. Such recombination is site-specific, the chromosomal location being determined by the fragment of chromosomal DNA carried on the suicide vector. (c) In the preferred method, the transposon containing an introduced DNA fragment and an antibiotic resistance gene may be transposed into the bacterial chromosome of the recipient gram negative bacterial strain. Selection for the antibiotic resistance ensures maintenance of the inserted DNA.

A further embodiment of the present invention is exemplified by the construction of a recombinant plasmid comprising a vector and a fragment of the symbiotic plasmid of *Rhizobium trifolii*. The invention is based on the unexpected discovery therein of DNA segments, herein designated RDS's. These three RDS's are designated RS-1(b), RS-2 and RS-3 (see below). In addition, a single RDS from a second strain of *Rhizobium trifolii* has been identified and sequenced. This RDS from the said second strain is designated RS-1(a) (see below).

RDS's isolated from rhizobial strains of the same species (e.g., *R. trifolii*) are substantially homologous with one another, but not with RDS's isolated from rhizobial strains of another species (e.g., *R. meliloti*. For example, a unique family of RDS's (see previous paragraph) is present in rhizobial strains capable of nodulating one or more species of clover. A plasmid comprising an RDS of *R. trifolii* can be used as a probe to identify unknown rhizobial isolates as clover-nodulating Rhizobia regardless of whether the strain was recovered from soil samples or from nodules of leguminous or non-leguminous plants. Similarly, RDS's of any other rhizobial species can be used to identify other members of that species. The isolation, characterization and method of using an RDS is described herein.

The isolation and recognition of RDS's of *R. trifolii* was achieved by isolation of the nif genes and the flanking sequences from the Sym plasmid of *Rhizobium trifolii*. Firstly, transposon-induced mutagenesis produced a variety of nif mutants and restriction fragments of the mutants carrying the transposon were cloned into various vectors and transformed into *E. coli* where they were amplified. Secondly, wild-type *R. trifolii* DNA was cleaved with restriction endonucleases and the cloned mutant nif gene fragments were radioactively labelled and used as probes to detect the wild-type nif fragments. Thirdly, these various wild-type nif fragments were radioactively labelled and used as probes to detect complementary sequences which were present in other regions of the Sym plasmid. Unexpectedly, it was discovered that multiple bands containing homologous sequences were detectable when certain nif fragments were used as probes. Mapping experiments showed the presence, on the 5' side of the nifH gene, of a DNA sequence which exists in at least 5–8 locations on the individual Sym plasmids of seven independent isolates of *R. trifolii* but not on the Sym plasmids of non-clover-nodulating Rhizobia.

In strain ANU843, the initially-isolated copy of the RDS, RS-1(b), was localized to a 1 kb region close to the 5' end of nifH. At least five copies of the RDS were found exclusively on the Sym plasmid of ANU843. No such sequence was detected in total DNA isolated from ANU845, a Sym plasmid-cured derivative of ANU843. A second copy of the RDS, RS-3, has been mapped approximately 28 kb distant from nifH. The uniqueness of this repeated sequence was shown by the fact that there was no detectable hybridization of this repeated sequence to the DNA of other rhizobial species, e.g., *R. meliloti* or *R. leguminosarum*. These two copies of the RDS, which have been mapped, flank a region which carries all of the identified nodulation and nitrogen fixation genes. This observation together with the fact that all copies of the RDS of *R. trifolii* are located on the Sym plasmid suggest that such sequences may play a role in the specificity of host-symbiont interaction during nodulation. Since an RDS is unique to rhizobial isolates that infect and nodulate a specific legume family, it can be used to quickly and efficiently identify other similar bacterial strains regardless of their origin. In principle, a recombinant plasmid comprising RDS (RDS plasmid, hereinafter) is constructed and amplified by replication in a host bacterial cell. Any host cell strain in which the RDS plasmid replicates is suitable for maintaining the plasmid and for generating adequate quantities of plasmid DNA. The plasmid itself may be derived from any stably-replicating plasmid vector capable of multicopy replication and bearing a genetic marker, such as a drug resistance gene, to permit selection of host cell lines carrying the plasmid.

Suitable host cell strains include, but are not limited to, strains of $E.\ coli$, Agrobacterium. Rhizobium and the like. Suitable plasmid vectors include, but are not limited to, narrow host range vectors such as pBR322, pACYC177, etc., and broad host range vectors such as pRK290, RP4, etc. The choice of plasmid vector and host will be matters of choice depending on considerations of operating convenience known and recognized by those of ordinary skill in the art.

An RDS plasmid can be radiolabelled by known means. Entire RDS plasmid DNA or a subfragment thereof comprising RDS, can be used as a hybridization probe to detect the presence or absence of DNA homologous to the RDS, in DNA extracted from a given rhizobial strain. The presence of DNA homologous to RDS indicates that the strain from which it was obtained will be capable of nodulating legumes of the family for which that RDS is diagnostic.

The hybridizations may be carried out on unfractionated DNA samples (dot-blot hybridization), or on electrophoretically fractionated DNA ("Southern" hybridization). The former is advantageous for screening large numbers of strains, while the latter is advantageous for locating specific fragments that contain RDS-homologous sequences. The most unequivocal identification of a given legume-nodulating strain will be obtained where hybridization is carried out under stringent hybridization conditions, as will be understood by those of ordinary skill in the art. The RDS is sufficiently long that stable hybrids will be formed even where flanking sequences are non-homologous. It will be understood that the most sensitive and specific hybridization will take place where the probe is the RDS itself, or a subfragment of the RDS plasmid containing the RDS.

By using the radioactively labelled probe pRt607 (see Examples), it was possible to identify and isolate four of the RDS DNA fragments from two strains of $R.\ trifolii$. Two of these fragments (RS-1(b) and RS-3) have been mapped at opposite ends of the region which carries all of the identified nodulation and nitrogen fixation genes while the position of the other fragment RS-2 has not been determined. Part of RS-1(a) has been mapped and sequenced at the 5'-end of the nifH gene of a second strain of $R.\ trifolii$. All four of these RDS fragments were partially sequenced and the results are given as follows (Table 2):

TABLE 2

```
RS-1 (a)  5'-TCTTCAGGA - GCGACA - G - - AT - - GTGACCAG - - TT
RS-1 (b)  5'-TCTTCAGGA - GCAACATGACAT - - GTGTCCGACATT
RS-2      5'-TCTTCAGGACTACTCACGACAT - - GTGTGCTACATT
RS-3      5'-TCTTCAGGG - GCA - CATGACATATGTG - - CGACATT

RS-1 (a)  GTCGTCACCTTTGTCGGCTTCGTG - ACACGCT - TTA
RS-1 (b)  GTCGTTTCCTTTGTCGACTTCGAG - ACACG - T - TTA
RS-2      GTCG - - - CCTTTGTCGACTTCGTGGACACG - TCTTA
RS-3      GTCGT       [ . . . unsequenced . . . ]

RS-1 (a)  GGATTCTTCGGTCCGGTATTTTATCCCTCTAAGTGT
RS-1 (b)  GGATTCTTCGGTCCGATATTTTATCTTTCTAAGTGT
RS-2      GGATTCTTCGGTCCGGTATTTTATCCCTCTAA - TGT

RS-1 (a)  CTGCGGCAGCACCAACTTCCGTTCTGCCCCTTCAAT
RS-1 (b)  TTGCGGCACA - CCAAATTCCGTTCTGCCACATCAAT
RS-2      TT - CGGCAGG - C - AAATTCCGTTCTGCCACATCAAT

RS-1 (a)  CAGCTCAAT - TGGCACCACGCTTGAAAATTGTTCTC
RS-1 (b)  CCGCCCAGTCTGGCACGACGCTTGAAAATTGTTCTC
RS-2      CCGCCCCGTCTGGCGC - ACGCTTGAAAATTGTTCTC

RS-1 (a)  GGGCTGCGACGGAACCACGCG - TCCGATGTCGCGGC
RS-1 (b)  GGGCTGCGACGGAACCAGCCGGTCCGATGTCGCG - -
RS-2      GGGCCGCGACGGAAGCA - - CGACTGCCAGTCGCGGC

RS-1 (a)  ATCCCCTGGGTCGATTCGAACACGAAAAGGAAGAAA
RS-1 (b)  ATCA - CTCGGTCGGTTCGA - CACGAAAAGGAAGCAA
RS-2      ATCACCTCGGTCGGTTCGAACACGAAAAGGAAGCAA

Met Ala Ala Leu Arg Gln ILe Ala Phe Tyr Gly
RS-1 (a)  TA  ATGGCTGCTCTGCGTCAGATCGCGTTTTACGGA

Leu
RS-1 (b)  TA  ATGCTTGCTCTGCGTCAGATCGCGTTTTACGGA

Ala
RS-2      TA  ATGGCTGCTCTCCGTCAGATCGCGTTTTACGGA

Lys Gly Gly Ile Gly Lys Ser Thr Thr Ser Gln Asn
RS-1 (a)  AAGGGAGGCATTGGCAAATCCACTACATCCCAGAAT
```

TABLE 2-continued

```
RS-1 (b)  AAGGGAGGCATTGGCAAATCCACTACATCCCAAAAT
RS-2      AAGGGAGGCATTGGCAAATCCACTACATCCCAAAAT
          THr Leu Ala Ala Leu Val Glu Leu Gly Gln Lys Ile
RS-1 (a)  ACGCTCGCTGCCCTCGTCGAACTTGGGCAGAAAATC
RS-1 (b)  ACGCTCGCTGCCCTTGTCGAACTTGGGCAGAAAATC

Pro
RS-2      ACGCCCGCCGCCCTTGTCGAA [ . . . not sequenced . . . ]

Leu Ile  Val Gly Cys Asp Pro Lys
RS-1 (a)  CTCATCGTCGGCTGCGACCCAAAA . . . .
RS-1 (b)  CTCATCGTCGGCTGCGACCCAAAG [ . . . not sequenced . . . ]
```

The experiments which provided the above data on the nucleotide sequences of RS-1(a), RS-1(b), RS-2 and RS-3 were repeated and extended. The results from these repeated experiments are given below as nucleotide sequences (Table 3) and as the predicted amino acid sequences from the open reading frames (Table 4). The codon (ATG) initiates the open reading frame (i.e., the first methionine residue). The sequences shown in Table 3 are continuous from end to end. However, in order to render the homologies more readily discernible and to keep totally homologous regions in register, gaps have been left in some sequences. It will be understood that such gaps are not intended to reflect physical discontinuities.

TABLE 3

```
RS-2                                         GATCTGCTTGCGCGCCT CTTCGGACTGCAGAAAGTTAACAAAACATGAGA
RS-3       CCGGTAAACCATAGCCATCCAGTCTCGCTAGAGAACAGCGCCGCTTTTCAAGGCCAGCAT

RS-1(a)                                 ATTGCTGCTCGATTGG  CGCTTCTACTCCGCG
RS-1(b)    ATCGATGCGCGGCTCATTCGACCGAGAGTTGTAGCGCATTGA  AGCCGACCCACTGCT
RS-2       CTGAAGATGCTCAAGGGATAATCGCGCGCTTCGAAAATGTTTGCGACAGGCCCCTCTGCT
RS-3       TTGCATCAAGTGCGCTCGATCGACCGAGAGGTGCGTCATTGG  GGCTSGCCCTCTGCGGC

RS-1(a)    GCCTCTTCAGGAGC          GACAGATGT   GACCAGTTGTCGTCACCTTTGTCGGCTTCGTG
RS-1(b)    TTCTCTTCAGGAGCAACATGACATGTGTCCGACA   TTGTCGTTTCCTTTGTCGACTTCGAG
RS-2       GTCTCTTCAGGATACTCACGACATGTGTGCGACA   TTGTCGTCAACTTTGTCGACTTCGTG
RS-3       T  TCTTCAGGGGCACCATGACATATGTGCGACA   TTGTCGT CGCTTTGTCGGCTTCGTG

RS-1(a)    ACACGCTTTAGGATTCTTCGGTCCGGTATTTTATCCCTCTAAGTGTCTGCGGCAGCACCAA
RS-1(b)    ACACGT CTTAGGATTCTTCGGTCCGATATTTTATCCCTCTAAGTGTTTGCGGCA CACCAA
RS-2       ACACGT CTTAGGATTCTTCGGTCCGGTATTTTATCCCTCTAAGTGTTTGCGGCAGCGCCAA
RS-3       ACACGGTTTAGGATTCTTCGGTCCAGTATTTTAAACCTCTAAGTGTCTGTGGCAGCACCAA

RS-1(a)    CTTCCGTTCTGCCCCTTCAATCAGCTCAAT TGGCACGACGCTTGAAAATTGTTCTCGGGC
RS-1(b)    ATTCCGTTCTGCCACATCAATCCGCCCAGTCTGGCACGACGCTTGAAAATTGTTCTCGGGC
RS-2       ATTCCGTTCTGCCACATCAATCCGCCCAGTCTGGCACGACGCTTGAAAATTGTTCTCGGGC
RS-3       CTTTCGTTCTGCCTA TCAATCAGCTCAAT TGGCACGACGCTTGAAAATTGTTCACGGGC

RS-1 (a)   TGCGACGGAACCA   CGCGTCCGATGTCGCGGCATCCCCTCGGTCGATTCGAACACGAAAA
RS-1 (b)   TGCGACGGAACCAGCCGCGTCCGATGTCGCGGCATCCCCTCGGTCGATTCGAACACGAAAA
RS-2       CGCGACGGAACCA   CGCGGCCGA GTCGCGGCATCACCTCGGTCGATTCGAACACGAAAA
RS-3       TGCGACGGAGCCGGCTTGTATGAAACGGAGATCAGCATGTCCATCCGAAAAA     GAAAG

RS-1 (a)   GGAAGAAATAATGGCTGCTCTGCGTCAGATCGCGTTTTACGGAAAGGGAGGCATTGGCAAA
RS-1 (b)   GGAAGCAATAATGGCTGCTCTGCGTCAGATCGCGTTTTACGGAAAGGGAGGCATTGGCAAA
RS-2       GGAAGCAATAATGGCTGCTCTGCGTCAGATCGCGTTTTACGGAAAGGGAGGCATTGGCAAA
R-3        TTCTTCGTCAAGCGGGGACAAGGCATCGTGTTTGGCAGCTTCAACGGAACTAAAACTGCGGAGACAAA

RS-1 (a)   TCCACTACATCCCAGAATACGCTCGCTGCCCTCGTC   GAACTTGGGCAGAAAATCCTCATCG
RS-1 (b)   TCCACTACATCCCAAAATACGCTCGCTGCCCTTGTC   GAACTTGGGCAGAAAATCCTCATCG
RS-2       TCCACTACATCCCAAAATACGCCCGCCGCCCTTGTC   GAACTTGGGCAGAAAATCCTCATCG
RS-3       CATGGAACCGGGTTTGAAAGCAGCGCT   CCTTGATCAGATCT

RS-1 (a)   TCGGCTGCGACCCAAAAGCTGA  TTCGACGCGATTGATCCTGAACTCCAAAGCGCAGGGCAC
RS-1 (b)   TCGGCTGCGACCC  AAAGGCTGA TTCGACGCGATTGATTCTGAACTCCAAAGCGCAGGGCAC
RS-2       CCGACTGCGACCC   AAAGACCGAGTTCACGCAATTGATCCTGTTTGCGAAAAAGAAAAAAGC
RS-3

RS-1 (a)   GGTTCTGGATCTAGCCGCAACGAAGGGTTCAGTTGAAGATCT   GGAACTCGGCGATGTGCTC
RS-1 (b)   TGTTCTGGATCTAGCCGCAACGAAGGGTTCAGTCGAAGATCT   GGAACTCGGCGACGTGCTC
RS-2       ATCCTTCGCAAAGCTC        AAGGACCAAAACATTTGCATTTGGGAATTC

RS-1 (a)   AAAACTGGCTACGGCGGCATCAAATGTGTGGAGTCGGGCGGCCCTGAACCCGGCGTCGGCT
RS-1 (a)   AAAACTGGCTACGGCGGCATCAAATGTGTGGAGTCGGGCGGCCCTGAACCTGGCGTCGGCT

RS-1 (a)   GCGCCGGACGGGGGGTCATAACGTCGATCAACTTCTTGGAAGAAAACGGCGCCTACGACGA
RS-1 (b)   GCGCCGGACGGGGCGTCATCACATCGATCAACTTCCTGGAAGAAAACGGCGCCTATGACGA
RS-1 (a)   TGTCGAC
RS-1 (b)   CGTCGAC
```

TABLE 4

| | | | | | | | | | | | | | | | | |
|---|---|---|---|---|---|---|---|---|---|---|---|---|---|---|---|---|
| RS-1(a) | Met | Ala | Ala | Leu | Arg | Gln | Ile | Ala | Phe | Tyr | Gly | Lys | Gly | Gly | | |
| RS-1(b) | Met | Ala | Ala | Leu | Arg | Gln | Ile | Ala | Phe | Tyr | Gly | Lys | Gly | Gly | | |
| RS-2 | Met | Ala | Ala | Leu | Arg | Gln | Ile | Ala | Phe | Tyr | GLy | Lys | Gly | Gly | | |
| RS-3 | Met | Gly | Pro | Gly | Leu | Lys | Ala | Ala | Leu | Leu | Asp | Gln | Ile | | | |
| RS-1(a) | Ile | Gly | Lys | Ser | Thr | Thr | Ser | Gln | Asn | Thr | Leu | Ala | Ala | Leu | Val | |
| RS-1(b) | Ile | Gly | Lys | Ser | Thr | Thr | Ser | Gln | Asn | Thr | Leu | Ala | Ala | Leu | Val | |
| RS-2 | Ile | Gly | Lys | Ser | Thr | Thr | Ser | Gln | Asn | Thr | Pro | Ala | Ala | Leu | Val | |
| RS-1(a) | Gly | Leu | Gly | Gln | Lys | Ile | Leu | Ile | Val | Gly | Cys | Asp | Pro | Lys | Ala | Asp |
| RS-1(b) | Gly | Leu | Gly | Gln | Lys | Ile | Leu | Ile | Val | Gly | Cys | Asp | Pro | Lys | Ala | Asp |
| RS-2 | Gly | Leu | Gly | Gln | Lys | Ile | Leu | Ile | Ala | Asp | Cys | Asp | Pro | Lys | Thr | Asp |
| RS-1(a) | Ser | Thr | Arg | Leu | Ile | Leu | Asn | Ser | Lys | Ala | Gln | Gly | Thr | Val | Leu | |
| RS-1(b) | Ser | Thr | Arg | Leu | Ile | Leu | Asn | Ser | Lys | Ala | Gln | Gly | Thr | Val | Leu | |
| RS-2 | Phe | Thr | Gln | Leu | Ile | Leu | Phe | Ala | Lys | Lys | Lys | Lys | Ala | Ser | Phe | |
| RS-1(a) | Asp | Leu | Ala | Ala | Thr | Lys | Gly | Ser | Val | Glu | Asp | Leu | Glu | Leu | Gly | Asp |
| RS-1(b) | Asp | Leu | Ala | Ala | Thr | Lys | Gly | Ser | Val | Glu | Asp | Leu | Glu | Leu | Gly | Asp |
| RS-2 | Ala | Lys | Leu | Lys | Asp | Gln | Asn | Ile | Cys | Ile | Trp | Glu | Phe | | | |
| RS-1(a) | Val | Leu | Lys | Thr | Gly | Tyr | Gly | Gly | Ile | Lys | Cys | Val | Glu | Ser | Gly | Gly |
| RS-1(b) | Val | Leu | Lys | Thr | Gly | Tyr | Gly | Gly | Ile | Lys | Cys | Val | Glu | Ser | Gly | Gly |
| RS-1(a) | Pro | Glu | Pro | Gly | Val | Gly | Cys | Ala | Gly | Arg | Gly | Val | Ile | Thr | Ser | Ile | Asn |
| RS-1(b) | Pro | Glu | Pro | Gly | Val | Gly | Cys | Ala | Gly | Arg | Gly | Val | Ile | Thr | Ser | Ile | Asn |
| RS-1(a) | Phe | Leu | Glu | Glu | Asn | Gly | Ala | Tyr | Asp | Asp | Val | Asp | | | | |
| RS-1(b) | Phe | Leu | Glu | Glu | Asn | Gly | Ala | Thr | Asp | Asp | Val | Asp | | | | |

It can be seen (Tables 2 and 3) that the nucleotide sequences of RS-1(a), RS-1(b), RS-2 and RS-3 are strongly conserved, substantially homologous and that they could be used to identify the symbiotic (Sym) plasmids of specific rhizobial isolates.

A number of other recombinant plasmids containing specific cloned fragments of nif DNA were constructed. The nifH promoter was cloned in pRt642; the N-terminal end of the nifH coding region was cloned in pRt669 and a nifHD specific fragment was cloned in pRt680.

A Southern blot of total R. trifolii strain ANU843 DNA was hybridized sequentially with radioactively-labelled insert fragments from each of the above recombinant plasmids. When hybridized with the nifH promoter probe pRt642, five or six positively-hybridizing bands were observed indicating that the repeated sequence is closely linked to, or is the nifH promoter. When the same blot was hybridized with the nifHD-specific probe pRt680, only a single positively-hybridizing fragment was observed, thus indicating that the DNA was completely digested and that only a single copy of the nifH and nifD genes was present in strain ANU843. Hybridization with the nifH-specific probe pRt669 showed that three copies of the N-terminal coding region of nifH were present.

The R. trifolii repeated sequences therefore fall into two classes. All copies are homologous with each other, but two of the sequences are linked to DNA homologous to the N-terminal end of the nifH structural gene. It is noteworthy that the repetitive sequences hybridize only within a rhizobial species and do not hybridize between species.

To locate other copies of the repeated sequence, the nifH promoter probe (pRt642) was used to screen a previously-constructed HindIII plasmid clone bank of R. trifolii ANU843 (Schofield, P. R. et al. (1983) Mol. Gen. Genet. 192:459-465). Two different recombinant plasmids were isolated from this bank. Restriction analysis showed that the plasmids contained inserts of 4.0 kb (pRt610) and 6.0 kb in size and they were designated as containing the second (RS-2) and third (RS-3) copies of this repeated sequence. The recombinant plasmid containing RS-3 was shown by restriction analysis to be plasmid pRt578, the insert of which is located approximately 30 kb to the right of the nifHDK genes on the ANU843 Sym plasmid (Schofield, P. R. et al. (1983) supra). The genes required for clover host-specific nodulation (Schofield, P. R. et al. (1984) Plant Mol. Biol. 3:3-11) are therefore flanked by two copies of the R. trifolii repeated sequence, namely RS-1(b) and RS-3.

The repeated sequence was further localized by Southern blot hybridization analysis of insert DNA of plasmids pRt610 and pRt578 and the RS-containing regions were sequenced.

To determine the occurrence of the repeated sequence among R. trifolii isolates, a number of geographically distinct strains were examined. Total DNA was extracted from strains isolated in Australia, the Middle East, the United Kingdom and the United States.

The DNA was restricted with EcoRI, Southern blotted and hybridized with radioactively labelled RS-1(b), i.e., pRt642. Autoradiographs indicated that repeated sequence were present in each of the R. trifolii isolates. Each strain examined had a unique pattern of hybridizing fragments indicating the usefulness of the RDS probe, e.g., RS-1(b), in distinguishing between various R. trifolii strains. These results showed that the repeated sequence was highly conserved in all the R. trifolii isolates examined. Therefore, other fast-growing rhizobial species were examined for the presence of this sequence. Total DNA was isolated from strains of R. trifolii, R. leguminosarum, R. meliloti, R. japonicum (a fast-growing species), Sesbania rhizobium, and a fast-growing cowpea Rhizobium.

Southern blot hybridization analysis of DNA of these strains with radioactively labelled RS-1(b) (pRt642) resulted in hybridization only being detected with R. trifolii DNA and not with the DNA isolated from any other rhizobial species. However, when the same Southern blot was rehybridized with the RS-1(b) and the nifH gene coding sequence (pRt608), positive hybridization to each of the rhizobial DNA's was observed. These hybridization data show that the *R. trifolii* repeated sequence, as exemplified by the *R. trifolii* RS-1(b) sequence, is unique to this species.

Conservation of the repeated sequence amongst geographically distinct *R. trifolii* isolates suggests that such sequences may play an important role in the ecology of this species. Indeed, the finding that the repeated sequences are located exclusively on the Sym plasmid in the seven *R. trifolii* strains examined, further supports this hypothesis. Analogous repeated sequences in *R. meliloti* are plasmid located (Better, M. et al. (1983) Cell 35:479-485). However, some copies are located on a second plasmid and not on the Sym plasmid.

Hybridization experiments have demonstrated that RS-1(b) is specific for *R. trifolii*. Ruvkun and Ausubel (Ruvkun, G. B. and F. M. Ausubel (1980) Proc. Nat. Acad. Sci. USA 77:191-195) have shown by hybridization analysis that the nitrogenase structural genes (nifDK) of diverse nitrogen-fixing microorganisms are highly conserved. However, the repeated sequences of the fast-growing rhizobial species do not show a high degree of interspecific homology. Thus, while the structural genes which constitute the nifDK operon appear to have been conserved in evolution, the repetitive sequences are evolutionarily divergent (at least among fast-growing, temperate legume-infecting rhizobial species). Considering the narrow plant host range shown by such fast-growing species, these observations suggest that species-specific repeated DNA sequences may be involved in host-specific expression of certain symbiotic genes.

In view of the species specificity of repetitive sequences, we suggest, but do not intend to be bound by, the following model for the activation of expression of nitrogen fixation genes in the fast-growing, temperate legume-infecting rhizobial species. According to the model, the appropriate species-specific repeated sequence is required for expression of the nifDK genes (and other species-specific, repeated sequence activated genes) by the appropriate rhizobial species which "normally" nodulates the given host plant. Thus, *R. trifolii* would only fix nitrogen in symbiosis with clovers if the nifDK and other repeated sequence-activated symbiotic genes carry the *R. trifolii* repeated sequences.

Under the conditions used in the present invention, the *R. trifolii* repeated sequences can be used as repetitive diagnostic sequences (RDS's) for both species and strain identification. A molecular approach to rhizobial taxonomy obviates the possible deleterious effects induced by using antibiotic markers for strain identification (Schwinghamer, E. A. (1964) Can. J. Microbiol. 10:221-233; (1967) Antonie van Leeuwenhock 33:121-136). The presence of analogous, but species-specific, repeated DNA sequences in other fast-growing rhizobial species will enable the rapid identification of other rhizobial species and unknown isolates.

EXAMPLES

Isolation of DNA

Genomic DNA was isolated from individual bacterial colonies as previously described (Scott, K. F. et al. (1981) J. Mol. Appl. Genet. 1:71-81). Extraction of DNA from liquid cultures was done by the same procedure except that the cell pellet from 5 ml culture was resuspended in 1 ml 25% sucrose in TE (10 mM Tris-HCl pH 8.0 1mM EDTA) and incubated for 30 minutes at room temperature with lysozyme (1 mg/ml) and EDTA (50mM). The suspension was diluted to 20 ml with TE and cells were lysed by the addition of SDS (to 0.4% w/v) and Pronase (100 $\mu$g/ml) with incubation at 37° C. for two hours. The lysate was extracted twice with phenol/chloroform (equal volume 1:1) and dialyzed against two changes of 0.3M NaCl in TE. DNA was precipitated with 2.5 volumes of ethanol at $-20°$ C.

For isolation of plasmid DNA, cultures were grown in L-broth and amplified by the addition of spectinomycin (250 $\mu$g/ml). Plasmid DNA was isolated by a polyoxyethylene ether-deoxycholate lysis procedure (Watson, J. et al. (1980) Plasmid 4:175-183). Cells from one liter cultures were harvested by centrifugation and resuspended in 10 ml cold 25% (w/v) sucrose in TE. After addition of lysozyme (3 mg/ml) and EDTA (200mM), the cells were lysed by the rapid addition of 15 ml 1% (v/v) polyoxyethylene ether 58, 0.4% (w/v) sodium deoxycholate in TE and incubation at 4° C, for 10-20 minutes. The lysate was centrifuged at 17,000 rpm for 40 minutes to pellet cellular debris. DNA was precipitated from the supernatant by the addition of 3% (w/v) NaCl and 1/4 volume 50% (w/v) polyethylene glycol 6000 with incubation on ice for at least 2 hours. After centrifugation at 5000 rpm for two minutes, the DNA pellet was resuspended in 5 ml 50mM NaCl in TE before addition of 8 g cesium chloride and 0.6 ml ethidium bromide (10 mg/ml) and incubation on ice for 30 minutes. Excess polyethylene glycol was removed by centrifugation at 10,000 rpm at 4° C. for 30 minutes. The density of the supernatant was adjusted to 1.59-1.61 g/ml by the addition of 1.5 ml 50 mM NaCl in TE. Plasmid DNA was banded by centrifugation at 100,000 g for 40 hours at 18° C.

Molecular Cloning and Hybridization

The construction of genomic libraries in the bacteriophage vector lambda-Charon 28 (Liu, C. P. et al. (1980) Science 209:1348-1353) and procedures used for screening libraries have been described previously (Scott, K. F. et al. (1982) J. Mol. Appl. Genet. 1:315-326).

Hybridization probes were prepared by the following and similar procedures all as known to the art, using primed synthesis with DNA polymerase I (Klenow fragment) using denatured random calf thymus DNA primers. Linearized plasmid DNA (100 mg) was heat-denatured by boiling for 2 minutes with 100 $\mu$g random primers (8-12 nucleotide fraction of DNAse I-treated calf thymus DNA) in 20$\mu$l and cooled on ice for 30 seconds. Denatured DNA was incubated for 30 minutes at 37° C. with 1 unit DNA polymerase I (Klenow fragment) in 10 mM Tris-HCl pH 7.4, 7-8 mM MgCl$_2$, 10 mM $\beta$-mercaptoethanol, 600 $\mu$M each of dGTP, dATP, and dTTP and 0.3 $\mu$M $\alpha$-$^{32}$P-dCTP ($>$3000 Ci/mmol, Amersham). The reaction was stopped by phenol/chloroform extraction and the aqueous phase passed over a Sephadex G-50 column to remove unincorporated radioactivity. Peak fractions (specific activity 107-108 cpm/$\mu$g DNA) were precipitated by the addition of *E. coli* tRNA (20 $\mu$g) and 2.5 vol. ethanol at $-20°$ C.

DNA was transferred from agarose gels and immobilized on nitrocellulose sheets by depurination, denaturation and blotting as described (Southern, E. M. (1975) J. Mol. Biol. 98:503-517).

DNA Sequencing

Sequence data was obtained by the use of both the chemical cleavage method (Maxam, A. M. and Gilbert, W. (1980) In Methods in Enzymol. 65, L. Grossman and K. Moldave, eds. (New York, Academic Press, pp. 499-560) and the chain termination method (Sanger, F.

et al. (1977) Proc. Nat. Acad. Sci. U.S.A. 74:5463–5467). For the latter procedure, template was generated by the construction of a series of defined deletions with the exonuclease Bal—followed by cloning into the bacteriophage vector M13mp8 as follows. Plasmid DNA (5 μg) was linearized with the endonuclease XhoI, digested with Bal—(20 units) in 20 mM Tris-HCl pH8.1, 12 mM CaCl$_2$, 600 mM NaCl and 1 mM EDTA at 31° C. Samples (10 μl) were taken at one minute time intervals and the digestion stopped by phenol-chloroform extraction and ethanol precipitation. The Bal—-digested DNA was then cleaved with EcoRI, ligated into EcoRI-HincII cleaved M13mp8 DNA and transformed into E. coli JM103 cells (Scott, K. F. et al. (1981) J. Mol. Appl. Genet. 1:71–81). Template DNA was isolated and sequenced.

Molecular cloning and DNA sequence of the nifH (fe-protein) gene from Rhizobium trifolii ANU329

Genomic DNA was isolated from R. trifolii ANU329 and partially cleaved with the restriction endonuclease Sau3A. The resulting DNA fragments were ligated into BamHI cleaved lambda-Charon 28 DNA and the phage DNA was packaged in vitro to generate an ANU329 library. This library was screened by hybridization with the 750 bp nifH specific fragment from pKnif-2 (Scott, K. F. et al. (1981) supra). DNA was prepared from the positively hybridizing recombinant (pRt329nif-3) and then cleaved with HindIII. The resultant HindIII restriction fragments were ligated into HindIII cleaved pBR322 and transformed into E. coli RR1. Recombinants were selected by hybridization to pKnif-2 sequences. DNA was prepared from the recombinant plasmid (pRt329nif-2) and sequenced by chemical and chain termination methods.

Expression of foreign genes under the control of a nif regulatory DNA region. Method I Construct a synthetic DNA primer which is complementary to the ribosome binding site of the ANU289 nifH gene (5'-CTCCATCAACCG-3'). Strain ANU289 is a streptomycin resistant strain of Bradyrhizobium sp. (Parasponia) derived from strain CP283. The nifH specific PstI-BamHI fragment which includes the nifH regulatory region (nifH-R.R.) is then subcloned into M13mp9, transformed into E. coli JM103 and incubated in 0.1M salt at 30° C. The cloned fragment is amplified and single stranded templates corresponding to the mRNA strand of ANU289 nifH are packaged and extruded into the media. The single stranded templates (ca. 1 μg) are recovered from the supernatant following centrifugation of the bacterial host. A 10-fold excess of the synthetic DNA primer in the presence of the four deoxynucleotide triphosphates (one of which is radioactive) and DNA polymerase I (Klenow fragment) is now used as a primer on this nifH template to generate double stranded DNA. The mixture is incubated for 15 minutes at 37° C. during which time more than 500 nucleotides are incorporated into the complementary strand. The remaining single stranded DNA is then removed by digestion with S1-nuclease. EcoRI linkers (CGAATTCC) are then ligated to the double stranded DNA fragments followed by digestion with EcoRI and PstI. The fragments are separated by agarose gel electrophoresis and the 567 base pair fragment is eluted and cloned into the wide host range plasmid pSUP204 or pSUP104, each of which has previously been restricted by the restriction enzymes PstI and EcoRI. The resulting recombinant plasmids are pSS204 and pSS104. Following transformation and amplification in a suitable E. coli host strain, e.g., SM10, cleavage with EcoRI allows the addition of any foreign structural gene or foreign DNA fragment into the linearized pSS204 or pSS104. For example, the human prolactin gene can be inserted (Cooke, N. et al. (1981) J. Biol. Chem. 256:4007–4016) or the human metallothionein gene can be inserted (Karin, M. and R. I. Richards (1982) Nucleic Acids Res. 10:3165–3173 and see the following Example) resulting in a co-integrated recombinant.

Following insertion of a foreign gene into linearized pSS204 or pSS104, the resulting co-integrated recombinant is transformed into a suitable E. coli host strain, e.g., SM10 or RR1. Subsequently the co-integrated recombinant is transferred to a rhizobial species, e.g., R. trifolii by bacterial conjugation using a helper plasmid such as RP4 if necessary. The rhizobial species carrying the co-integrated recombinant is then used to infect plants and later the root nodules are assayed for the production of foreign mRNA and/or protein by standard methods known in the art.

Insertion of the human metallothionein gene into the recombinant plasmid pRK290-nifH-R.R. Method II The procedure followed in this example is the same as that followed in the preceding Example up to the point where EcoRI linkers are ligated to the double stranded DNA fragments followed by digestion with EcoRI and Pst. The resultant DNA fragments (approximately 567 base pairs) are then cloned into EcoRI-PstI cleaved pBR322. Following transformation and amplification in a suitable E. coli host strain, the recombinant plasmids are cleaved with PstI and treated with S1 nuclease for a short time to remove the 3'-overhang. The recombinants are then cleaved with EcoRI and the double stranded nif regulatory fragment is cloned into SmaI-EcoRI cleaved pRK290 DNA. The resultant recombinant is thus a pRK290-nif-regulatory fragment construct (pRK290-nifH-R.R.). pRK290 is a wide host range plasmid.

The next step is to isolate DNA fragments carrying the foreign genes of interest and to ligate synthetic EcoRI linkers to these fragments. These modified fragments are then ligated into EcoRI cleaved vector DNA (i.e., the pRK290-nif regulatory fragment constructs) giving a co-integrated recombinant (pRK290-nif regulatory fragment-foreign gene) and transformed into an E. coli host strain, e.g., SM10 or RR1. The co-integrated recombinant is then transferred to a rhizobial species by bacterial conjugation using a helper plasmid whenever necessary. The rhizobial organisms carrying the co-integrated recombinant are then used to infect plants and later assayed for the production of foreign mRNA and/or protein by standard methods known in the art.

Insertion of the human metallothionein gene into the recombinant plasmid pSS104

Total RNA was extracted from HeLa cells (Chirgwin, J. M. et al. (1979) Biochemistry 18:5294–5299) which had been maximally induced to synthesize metallothionein by incubating in $10^{-5}$M cadmium chloride plus $10^{-4}$M cycloheximide for eight hours before harvesting (Karin, M. et al. (1981) Eur. J. Biochem. 18:527–531). Poly-A containing RNA was selected by hybridization to oligo(dT)-cellulose (Aviv, H. and P. Leder (1972) Proc. Nat. Acad. Sci. U.S.A. 69:1408–1412) and used as template for the synthesis of double stranded cDNA by sequential reverse transcriptase reactions. The hairpin bends were removed by S1 nuclease digestion and then homopolymeric dCMP tails were added to the 3'-termini of the cDNA by incubation with terminal transferase and dCTP (Chang, A. C. Y. et al. (1978) Nature 275:617-624). The double-stranded dCMP-tailed cDNA sequences were annealed to plasmid pBR322 DNA, previously linearized with restriction endonuclease PstI and tailed at the 3' ends with dGMP residues. The resulting recombinant plasmid DNA was used to transform E. coli RRI. Colonies carrying the recombinant plasmid were recognized by their $Amp^s$, $Tet^r$ phenotype. Bacterial colonies containing recombinant plasmids were grown and fixed on 0.45 μ nitrocellulose filters (Grunstein, M. and D. S. Hogness (1975) Proc. Nat. Acad. Sci. U.S.A. 72:3961-3965). Duplicate filters were hybridized with $^{32}$P-labelled cDNA synthesized from poly-A containing mRNA from either induced or uninduced HeLa cells (see supra). Colonies which were judged by radioautography to give a stronger hybridization signal with induced cDNA were selected. A second test was by hybridization to a cloned mouse metallothionein-I cDNA clone (Durnam, D. M. et al. (1980) Proc. Nat. Acad. Sci. U.S.A. 77:6511-6515). The positive clones were finally verified as human metallothionein genes by nucleic acid sequence analysis.

The human metallothionein recombinant clone is then restricted with NcoI and the overhangs are filled in to blunt ends (Maniatis, T. Jeffrey, A. and D. G. Kleid (1975) Proc. Nat. Acad. Sci. U.S.A. 72:1184-1188). EcoRI linkers are then added to these blunt ends and the fragment is inserted into pSS104 as shown above. Those co-integrated recombinants carrying the human metallothionein gene are transformed into an E. coli strain, e.g., SM10, and subsequently transferred to a rhizobial species by bacterial conjugation. Rhizobial organisms carrying the co-integrated recombinant are used to infect plants and the expression of the metallothionein gene in the root nodules is monitored by detection of mRNA and/or protein synthesis by standard methods known in the art.

Insertion of the bacterial toxin gene from Bacillus thuringiensis into the recombinant plasmid pSS204

Recombinant plasmids containing inserts of the gene encoding the toxic crystal protein of B. thuringiensis are obtained using the techniques described (Wong, H. C. et al. (1983) J. Biol. Chem. 258:1960–1967). The recombinant plasmid pES1 (ATCC Number 31995) consisting of the plasmid vector pBR322 and DNA homologous to the 30, 32 and 37 megadalton plasmids, as well as DNA homologous to linearized forms of the very large plasmids of *B. thuringiensis* is partially cleaved with EcoRI to give linear molecules. These partial cleavage products are further restricted by the enzyme AvaI. The digestion conditions are as recommended by the manufacturer. A probe for the toxic crystal protein gene is isolated and radioactively labelled as previously described (Wong, H. C. et al. (1983) see supra). The restriction fragments are separated by agarose gel electrophoresis and the labelled probe is found to hybridize to one fragment of approximately 15 kilobases (kb). This fragment includes the EcoRI fragments D and F (Wong et al., supra). The 15 kilobase fragment is then cloned into M13mp8 or M13mp9 according to standard procedure (Messing, J. and J. Vieira (1982) Gene 19:269–276) and transformed into *E. coli* JM103. The single stranded DNA from the extruded phage particles is purified and replicated in-vitro by use of a synthetic primer (5′-TGTTATCCATGGGTTACCTCC-3′). (The general method of site specific mutagenesis is described in Zoller, M. J. and M. Smith (1982) Nucleic Acids Research 10:6487–6500.) The resulting double-stranded recombinant plasmid is then transformed back into *E. coli* JM103 and amplified. The amplified double-stranded plasmid DNA is purified from the *E. coli* JM103 cells and cleaved with the restriction endonuclease NcoI and AvaI. NcoI cleaves at the site of the synthetic primer (which is the initiation site of the toxic crystal protein gene) and AvaI cleaves at a site which is downstream from the 3′-end of the toxic crystal protein gene. The overhangs are then filled in to blunt ends (Maniatis, T. et al. (1975) supra). Finally the pSS204 recombinant plasmid which is derived from pSUP204 is cleaved with EcoRI and the overhangs filled in to blunt ends. HindIII linkers are then added to both the *B. thuringiensis* toxic crystal protein gene fragment and to the pSS204 recombinant. Following the HindIII digestion of both components, the toxic crystal protein gene and the pSS204 recombinant plasmid are ligated together to give a pSS204-*B. thuringiensis* toxic crystal protein gene cointegrate. The mixture is transformed into a suitable *E. coli* host, e.g., K802, SM10 or RR1. Plasmids are isolated from individual colonies and the orientation determined by restriction mapping. A colony containing a plasmid with the correct orientation is then conjugated to a rhizobial strain and the plasmid is transferred as already described. The production of mRNA and/or the toxic crystal protein is monitored as already described (Wong et al., supra).

Introduction of DNA sequences into the genome of gram-negative organisms other than *E. coli*

This example is based on the following general principles. Two basic components are required. These are: (1) a suicide vector, and (2) a transposon.

Suicide vectors are plasmid molecules which replicate stably in one bacterial host (in this case, *E. coli*) but fail to replicate in a different bacterial species (e.g., *Rhizobium trifolii*). Transposons are genetic elements which are able to move (translocate) from one location to another in DNA. The translocation process is mediated by gene products encoded on the transposon and is dependent upon the integrity of repeated sequences (directly or indirectly repeated) located at each end of the transposon. Transposons generally carry a gene (or genes) encoding resistance to one or more antibiotics.

In the protocol to be outlined below, use is made of the transposon designated Tn5 and the suicide vector pSUP1011 (Simon, R., Priefer, U. and A. Puhler (1981) Proc. of Bielefeld Symposium. Springer-Verlag, West Germany). Transposon Tn5 is a DNA element of 5.7 kilobases (kb) in length, consisting of 1.5 kb inverted repeat sequences flanking a 2.7 kb central region. Encoded within one of the inverted repeats are the functions required for transposition. The central region of the transposon carries a gene conferring resistance to the antibiotic kanamycin (Kmr). In the middle of central region is a DNA sequence which is recognized by the restriction endonuclease BamHI In the suicide vector pSUP1011, the only site recognized and cut by BamHI is that located within the Tn5 element. Experiments (Simon, R., Priefer, U. and A. Puhler (1983) Proc. of Bielefeld Symposium, Springer-Verlag, West Germany) have shown that insertion of DNA fragments into the BamHI site of Tn5 does not disrupt normal transposition nor expression of the kanamycin-resistance gene of the resultant "hybrid" transposon.

The DNA fragment to be introduced can be generated in a number of ways:

1) Complete or partial restriction with BamHI, Sau3A, MboI, etc. which generates fragments having the same, complementary, single-stranded ends.

2) Partial or complete digestion with restriction endonucleases which generates DNA fragments having blunt ends.

3) Digestion of DNA with the enzyme DNAseI in the presence of Mn++ ions which generates random fragments which (generally) are blunt ended.

The suicide vector (pSUP1011) DNA is treated as follows depending on the type of fragment to be cloned (above):

1) Complete restriction with endonuclease BamHI and treatment with the enzyme alkaline phosphatase.

2) Complete restriction with BamHI followed by either:
a) treatment with S1 nuclease to remove the single-stranded ends, or
b) "filling in" of the single-stranded ends by the enzyme reverse transcriptase in the presence of nucleotide triphosphates.

Each of the above treatments is followed by treatment with alkaline phosphatase.

Cloning: Vector and fragment DNA, prepared as above, are mixed and treated with the enzyme T4 DNA ligase. The ligated DNA is then transformed (introduced) into *E. coli* strain SM10. (This strain is capable of mobilizing (Mob+) pSUP1011 derivatives (recombinant plasmids) into other gram-negative bacteria.) (Simon, R., Priefer, U. and A. Puhler (1983) Proc. of Bielefeld Symposium. Springer-Verlag, West Germany). The resultant transformants are screened by the Grunstein and Hogness colony hybridization procedure (Grunstein, M. and D. S. Hogness (1975) Proc. Nat. Acad. Sci. U.S.A. 72:3961) to detect those containing the desired cloned DNA fragment.

Introduction of the cloned DNA fragment into the genome of any gram-negative bacterium (e.g., *R. trifolii*) is achieved via a process called bacterial conjugation. The *E. coli* SM10 derivative, carrying the desired pSUP1011 recombinant, is mixed with cells of (kanamycin-sensitive) *R. trifolii* on the surface of a nutrient agar plate. The plate is incubated for a period (4–16 hours) at 29°–30° C. (optimum temperature for *R. trifolii*) and during this time cells of each type come into physical contact (conjugation) and the pSUP1011 derivative is transferred from *E. coli* to *R. trifolii*. The cell mixture is washed off the plate and spread on an agar plate which is selective for kanamycin-resistant *R. trifolii*. The resultant colonies will be derivatives of *R. trifolii* in which the cloned DNA fragment, within Tn5, will be inserted at some point in the genome. Selection for kanamycin resistance ensures maintenance of the inserted DNA.

At this stage it is unknown whether the DNA fragment, within Tn5, has been transferred to the chromosome of *R. trifolii* or to one of its several plasmids. This uncertainty can be resolved by visualization of the plasmids and the bacterial chromosome by ethidium bromide staining after horizontal agarose gel electrophoresis (Djordjevic, M. A. et al. (1982) J. Bacteriol. 151:560-568).

Isolation of a DNA fragment containing one or more nodulation genes

Total *R. trifolii* DNA was prepared by harvesting 10 ml of cells (O.D$_{650}$=0.5) grown at 30° C. with aeration in TY broth (Beringer, J. E. (1974) J. Gen. Microbiol. 84:188-198). The cell pellet was washed twice in 3 ml of TES (10 mM Tris, pH 8.0; 1 mM EDTA; 100 mM NaCl) and resuspended in 1 ml of TE (10 mM Tris, pH 8.0; 1 mM EDTA). 0.2 ml of fresh lysozyme (5 mg/ml in TE), 0.4 ml of 0.25M EDTA were added and incubated at 37° C. for 30 minutes. 0.5 ml of pronase (1 mg/ml in TE) and 0.1ml of 20% SDS were added and the digest was incubated at 37° C. for 60 minutes. The digest was extracted four times with 4 ml of phenol:chloroform (1:1). The two phases were separated by centrifugation (20,000 rpm, 20 minutes, SS-34 rotor). The DNA was precipitated with 2.5 vol. of −20° C. ethanol and 0.1 vol. of 3M sodium acetate, pH6.0 at −70° C. for 30 minutes. After centrifugation the DNA precipitate was redissolved in 1 ml of TE and dialyzed against three changes of TE buffer.

Following restriction with the appropriate endonuclease in TA buffer (O'Farrell, P. H. et al. (1980) Molec. Gen. Genet. 179:421-435), DNA was electrophoresed in 1% horizontal TAE (40 mM Tris; 20 mM sodium acetate; 2 mM EDTA, pH 7.8) agarose gels (4 x 140 x 190 mm) at 40 volts for 16–18 hours. After transfer to nitrocellulose (Southern, E. M. (1975) J. Molec. Biol. 98:503-517), the DNA was hybridized to 10$^7$ cpm of an [α$^{32}$P]dCTP-labelled probe prepared by the method of random priming (Whitfeld, P. L. et al. (1982) DNA 1:133-143) at 65° C. for 16 hours.

The probe used was pRt851 (a Rhizobium DNA fragment containing a Tn5 insertion from ANU851 cloned in the vector plasmid pBR322). Tn5 mutagenesis of *R. trifolii* wild type strain ANU843 has previously been used to isolate mutants defective in many of the steps leading to symbiotic nitrogen fixation (Scott, K. F. et al. (1982) J. Mol. Appl. Genet. 1:315-326). The majority of these mutants can still initiate nodule development but are defective in one of the later steps of the symbiosis, such as release of bacteria from the infection thread, bacteroid development or nitrogen fixation. The Tn5-induced mutant of *R. trifolii* ANU851 used as a probe in this example is a stable nodulation deficient (Nod-) phenotype and is unable to induce clover root hair curling (Hac-), an early stage in nodule development (Rolfe, B. G. et al. (1981) in "Current Perspectives in Nitrogen Fixation", Gibson, A. H. and W. E. Newton, eds. pp. 142-145 Australian Academy of Science, Canberra). Southern blot analysis (Southern, E. M. (1975) J. Molec. Biol. 98:503-517) of DNA from the Hac- mutant ANU851 showed the presence of a unique band of approximately 13 kb (5.7 kb of Tn5 inserted into a 7.2 kb EcoRI restriction fragment) that hybridized to Tn5 sequences. This confirmed that a single Tn5 insertion was responsible for the Hac- phenotype of ANU851. The 13 kb DNA fragment containing Tn5 and flanking *R. trifolii* sequences was isolated from ANU851 by restriction of total DNA with EcoRI and molecular cloning into the *E. coli* plasmid pBR322 to give the recombinant plasmid pRt851.

Construction of clone banks of rhizobial DNA

Clone banks of *R. trifolii* strain ANU843 were constructed in the plasmid cloning vector pBR328 (Soberon, X. et al., (1980) Gene 9:287). Vector DNA was digested to completion with the restriction endonuclease EcoRI, HindIII or BamHI in TA buffer (O'Farrell et al. (1980) Molec. Gen. Genet. 179:421-435). After inactivating the restriction enzymes by phenol:chloroform (1:1) extraction, the DNA was ethanol precipitated, pelleted by centrifugation and dried in vacuo. The restricted vector DNA was reconstituted in 0.1M Tris base, pH 10-11, containing 0.2% sodium dodecyl sulfate and 0.1–0.2 units of calf intestinal alkaline phosphatase per μg of DNA. The reaction mixture was incubated at 37° C. for one hour, extracted three times with an equal volume of phenol: chloroform (1:1), ethanol precipitated, dried in vacuo and reconstituted at a concentration of 500 μg/ml in TE buffer.

Total DNA (5-10 μg), derived from R. trifolii was digested to completion with EcoRI, HindIII or BamHI in TA buffer. Reactions were terminated by heating the digests at 65° C. for 15 minutes. The DNA was then ethanol precipitated, dried and reconstituted in a final volume of 20-50 μl containing 10 mM Tris, pH 7.4, 8 mM MgCl$_2$, 10 mM β-mercaptoethanol, 1 mM ATP and 0.5 μg of appropriately-digested, alkaline phosphatase-treated pBR328 DNA. After the addition of 5 units of T4 DNA ligase, the mixture was incubated at 20-25° C. for 3-4 hours.

Ligated DNA (equivalent to 100-200 ng of pBR328) was diluted to 100 μl with TE buffer and transformed into 200 μl of preserved competent cells of E. coli strain RR1 (Morrison (1977) J. Bacteriol. 132:349).

Transformants were selected on L agar (Miller, (1972) Experiments in Molec. Biol., Cold Spring Harbor Lab, New York) containing 50 μg of ampicillin per ml. The frequency of recombinant plasmids was assessed by spotting 100-200 transformant clones to L agar containing 50 μg of chloramphenicol per ml (for EcoRI clones) or 25 μg of tetracycline per ml (for HindIII or BamHI clones).

Generally, 90-95% of the transformants contained recombinant plasmids as indicated by insertional inactivation (Timmis et al. (1974) Proc. Nat. Acad. Sci. U.S.A. 71:4556).

Isolation of Wild-type Nod Genes

Wild-type ANU843 DNA was cleaved with various restriction endonucleases and cloned as described in the above Example, and the hybridization probe described in the above Example was used to detect wild-type nod genes. When pRt851 was used as the hybridization probe and EcoRI as the restriction endonuclease, a 7.2 kb wild-type EcoRI restriction fragment was recovered. This was cloned into pBR328 to yield recombinant plasmid pRt572. If HindIII was used as the restriction enzyme, a 14kb wild type HindIII restriction fragment was recovered. This was also cloned into pBR328 to yield recombinant plasmid pRt587. These two recombinant plasmids (pRt572 and pRt587) were then used as probes in a "walk" to detect overlapping recombinant clones derived by cleavage with a different restriction endonuclease. In this manner, various fragments covering 27 kb DNA spanning all the nif and nod genes and the adjacent flanking sequences were recovered and mapped. The various fragments were isolated by cloning into the vector plasmid pBR328 (Soberon, X. et al. (1980) Gene 1:287-305) and transformed into E. coli RRI. RS1 and RS3 are seen to be included within the fragments pRt585 and pRt578, respectively.

Preparation of hybridization probes

Radioactive probes were prepared by primed synthesis using random 8-12 nucleotide long oligonucleotide primers made from calf thymus DNA. Template DNA (100-200 ng purified restriction fragment, or 1-2 μg linear plasmid DNA) and 100 μg primer were mixed in 20 μl H$_2$O, denatured by boiling for 2 minutes and quick cooled on ice. Synthesis was initiated by the addition of 50 mM Tris-HCl pH 8.0, 20 mM KCl, 7 mM MgCl$_2$, 10 mM β-mercaptoethanol, 600 μM dGTP, 600 μM dTTP, 600 μM dATP, 0.3 μM α$^{32}$P-dCTP (3000 Ci/mmole, Amersham) and 5 units E. coli DNA polymerase I (Klenow fragment). This mix was incubated at 37° C. for 30 minutes. For probes with higher specific activities the 600 μM dATP was replaced with 0.3 μM β$^{32}$P-dATP (3000 Ci/mmole). The reaction was stopped with 25 mM EDTA and extracted with phenol and chloroform.

To separate the unincorporated nucleotides from $^{32}$P-labelled DNA, the aqueous phase was loaded onto a Sephadex G-50 column (5cm×9mm) and washed through with TEN buffer (0.1 M NaCl, 10 mM Tris-HCl pH 8.0 and 1 mM EDTA). Fractions (3-4 drops, 200-500 μl) were collected and the void fractions containing radioactively labelled DNA (as monitored by a Geiger counter-mini meter) were pooled. E. coli tRNA (30 μg) was added as a carrier and the DNA was recovered by ethanol precipitation. Probes were denatured by boiling for 2 minutes before use Specific activities obtained generally ranged from $1 \times 10^7$ to $9 \times 10^7$ cpm/μg template DNA.

Detection of repetitive sequences in the Sym plasmid

When certain of the fragments cloned into the vector plasmid pBR328, e.g., recombinant plasmids pRt585 and pRt578 (see the above example describing construction of clone banks of rhizobial DNA), were radioactively labelled and used as hybridization probes against restricted wild-type ANU843 DNA, it was found that they hybridized to several different bands, thus demonstrating repetitive sequences. These complementary fragments were not located on the bacterial chromosome because no complementation occurred when the hybridization test was done with similarly-restricted DNA from ANU845. ANU845 is a derivative of ANU843 and differs from that strain by the loss of the Sym plasmid, i.e., it has been "cured" of the plasmid. These recombinant plasmids (pRt585 and pRt578) were amplified and purified. They were then radioactively labelled and used as probes to test for the presence of the symbiotic (Sym) plasmid in other isolates of R. trifolii and other species such as R. meliloti and R. leouminosarum.

Detection of the Sym plasmid and of RDS in isolates of Rhizobia

The strain to be tested was grown in culture and the DNA was isolated. Alternatively the DNA from the various plasmids was isolated and the Sym plasmid was purified (Hooykaas, P. J. J. et al. (1981) Nature 291:351). The DNA to be tested was then suitably restricted and the fragments separated by agarose gel electrophoresis (Aaij, C. and P. Borst (1972) Biochem. Biophys. Acta. 269:503-517). The electrophoresed DNA fragments were then transferred to nitrocellulose filters (Schleicher and Schull, BA85) (Lawn, R. M. et al. (1978) Cell 15:1157-1174) and the double stranded DNA probes (e.g., pRt585 or pRt578) were radioactively labelled by nick translation (Rigby, P. W. J. et al. (1977) J. Mol. Biol. 113:237-251). It will be readily apparent to those skilled in the art that if the DNA to be tested and the probe were obtained by use of the same restriction enzyme, then a minimum value for the number of RDS's in a symbiotic (Sym) plasmid can be determined.

The nitrocellulose filters containing immobilized Sym plasmid DNA restriction fragments were prehybridized for two hours at 65° C. in 3×SSC (0.45M NaCl, 0.045M Na-citrate), 50 mM HEPES pH 7.0 (N-2-hydroxyethylpiperazine-N' -2-ethanesulfonic acid), 0.1% (w/v) NaDodSO$_4$ (sodium dodecyl sulfate), 0.2% (w/v) each polyvinylpyrrolidone (PVP), Ficoll, bovine serum albumin (BSA), 20 μg/ml denatured and sheared herring sperm DNA, and 20 μg/ml *E. coli* tRNA before addition of approximately 1×10⁶ cpm probe DNA per filter. Hybridization was carried out for 18-24 hours at 65° C. Filters were washed in 2×SSC and 0.1% NaDodSO₄ at room temperature for two hours before exposing to X-ray film (Kodak XS-5) in the presence of an intensifying screen (Dupont Cronex lightning plus) at −70° C. for 1-3 days. If RDS's are present on the Sym plasmid or the restricted DNA, then more than one band will "light up" on the autoradiograph.

When labelled pRt585 or pRt578 were used as probes, multiple bands of Sym plasmid DNA were labelled, indicating that these probes included a common sequence (RDS). The multiple bands were more readily observable at longer exposure times. Multiple bands were not observed when other probes (e.g., pRt572) were used, nor were multiple bands observed when the RDS-containing probes were hybridized to Sym plasmid DNA from other rhizobial species, e.g., *R. meliloti*.

Construction of a probe containing RS-1(b)

Digestion of the Sym plasmid of *R. trifolii* with the restriction enzyme ClaI yielded a DNA fragment which comprises the RS-1(b) RDS and the nifH gene. The ends of this fragment occurred 50-60 base pairs to the left of RS-1(b) and at an undefined distance to the right of the nifH gene. This Sym plasmid ClaI fragment was inserted into the ClaI site of pBR328. Insertion may occur in either orientation, and insertions in both orientations were recovered.

The Sym plasmid ClaI fragment contained an AvaI site immediately to the left of the nifH gene and pBR328 contains a single AvaI site. The recombined pBR328 plasmid (i.e., pBR328+the Sym plasmid ClaI fragment) was cleaved with AvaI, a different DNA fragment being deleted depending on the insertion orientation. In one orientation the RS-1(b) sequence was deleted (pRt608) while in the other orientation the nifH gene was deleted (pRt642). Following deletion of the nifH gene, the recombinant plasmid pRt642 contained RS-1(b), about 50-60 bp to the left of RS-1(b) and about 200 bp to the right of RS-1(b). Recombinant plasmid pRt642 would then be used as a probe to more precisely locate the positions of the RDS segments on any symbiotic plasmid of any rhizobial isolate.

A general method for the isolation of Rhizobium Diagnostic Segments (RDS's)

An RDS is defined as a member of a family of substantially homologous DNA sequences specific to a given rhizobial species. In turn, a substantially homologous DNA sequence is defined in terms of the conditions which permit hybridization of denatured DNA fragments as described in this example.

The presence of an RDS is detected when a cloned DNA fragment, of given size, is radioactively labelled and hybridized to restriction fragments of total DNA (cut with the same enzyme as was used for cloning). Normally only one positively-hybridizing fragment, namely that corresponding to the cloned probe fragment will be seen. However, if the probe includes an RDS, then additional positively-hybridizing bands will be seen.

Further proof for the presence of an RDS is obtained by subdividing the original fragment into smaller subfragments with a second restriction enzyme. When each of the subfragments is radioactively labelled and separately probed onto restriction fragments of total DNA (generated by the original cloning enzyme), then each will hybridize to the original cloned fragment. However, one or more of the subfragments will also hybridize to the multiplicity of fragments observed when the entire fragment is used as a probe. In this way the RDS can be mapped and probes prepared which are mostly RDS with a minimum of flanking DNA.

It will be noted from this description that repeated sequences are not cloned directly but are found on fragments which have already been cloned. In this case, the cloned fragments were obtained from a plasmid clone bank of *R. trifolii* strain ANU843 DNA fragments.

More specifically, total DNA was isolated from eight independent isolates of *R. trifolii* and one strain of *R. meliloti* by the method of Schofield et al. (1983) Mol. Gen. Genet. 192:459–465. The resultant total DNA's were restricted completely with the restriction endonuclease EcoRI in TA buffer (O'Farrell et al. (1980) Molec. Gen. Genet. 179:421–435) and electrophoresed in 1% horizontal TAE (40 mM Tris:20 mM sodium acetate:2 mM EDTA, pH 7.8) agarose gels (4×140×190 mm) at 40 Volts for 16–18 hours. DNA fragments were transferred to nitrocellulose (Southern, E. M. (1975) J. Molec. Biol. 98:503–517) and hybridized to 10⁷ cpm of an α-³²P-dCTP labelled probe (pRt607) prepared by the method of random priming (Whitfeld, P. L. et al. (1982) DNA 1:133–143) at 65° C. for 16 hours. It will be understood by those skilled in the art that temperatures lower than 65 and/or times longer than 16 hours will decrease the stringency of the hybridization conditions and that the length and degree of complementarity of the DNA under consideration will also affect the extent of hybridization. RDS's from different locations on the same Sym plasmid are sufficiently self-complementary to hybridize under the described conditions and under less stringent conditions. However, under less stringent conditions, the likelihood of false positive results increases. The recombinant plasmid, pRt607 is a derivative of pBR328 (Soberon, X. et al., supra) which contains a 1 kb ClaI fragment, derived from the Sym plasmid of *R. trifolii* strain ANU843, on which the repeated sequence RS-1(b) and part of the nifH structural gene are located. The nitrocellulose was washed three times for 15 minutes in 2×SSC (standard saline citrate) at 65° C. and exposed to X-ray film (Kodak XAR-5) in the presence of an intensifying screen (Dupont Cronex Lightning Plus) at −70° C. for 2 days. Multiple bands were shown for all *R. trifolii* isolates, but not for the *R. meliloti* isolate.

Alternatively, the probe Rt607 can be made smaller and more specific by cleaving with the restriction enzyme AvaI, which will remove the nifH portion of the probe and a non-essential DNA sequence of pBR328. Following religation, a plasmid designated pRt642 comprising the repeated sequence RS-1(b) is recovered. This more specific probe pRt642 can be used as described above to detect substantially homologous RDS.

Isolation of RDS of the symbiotic Sym) plasmid of Rhizobium meliloti

Cells of *R. meliloti* are grown and harvested as described above. Then the DNA from the various plasmids is isolated and the Sym plasmid is purified (Hooykaas, P. J. J. et al. (1981) Nature, London 291:351). The DNA to be tested is then suitably restricted, e.g., by EcoRI, and the fragments are separated by agarose gel electrophoresis (Aaij, C. and P. Borst (1972) Biochim. Biophys. Acta. 269:503-517). The electrophoresed DNA fragments are transferred to nitrocellulose filters (Schleicher and Schull, BA85) (Lawn, R. M. et al. (1978) Cell 15:1157–1174).

The identical DNA which is to be tested (see previous paragraph) is then again restricted with the same enzyme, i.e., EcoRI, and a number of the fragments are cloned into a suitable vector, e.g., pBR322, transformed into a suitable host, e.g., *E. coli* HB101, and amplified. Following amplification, the plasmid is purified and the inserted fragment excised with EcoRI. These double-stranded DNA fragments ar then radioactively labelled by nick translation (Rigby, P. W. J. et al. (1977) J. Mol. Biol. 113:237–251) and used as probes to detect substantially homologous RDS's separated by electrophoresis and transferred to nitrocellulose filters as described in the previous paragraph. Hybridization conditions are the same as described in the preceding Example. It will be obvious that the probe is homologous to at least the one corresponding fragment of the DNA to be tested since both are digested by the same restriction enzyme. If the DNA in the probe represents a unique sequence, then only one band will "light up" following hybridization and autoradiography; whereas if the probe comprises an RDS, then a number of bands corresponding to the various RDS's of that symbiotic (Sym) plasmid will light up. In the latter case, the cloned probe fragment is maintained and can be used to detect substantially homologous RDS's from rhizobial isolates obtained from soil samples or from root nodules. The procedure is repeated with other restriction enzymes, giving similar multiple bands in response to a probe comprising RDS. Control hybridizations using an RDS probe of another rhizobial species (e.g., pRt642) demonstrates lack of substantial homology between RDS's of the two species. It will be understood that a control probe from another species may hybridize with one of the DNA fragments if the probe is large enough to include sequences flanking the RDS's that are conserved between the species. Such a result was observed when pRt585 was used to probe *R. meliloti* DNA. In that instance, the presence of part of nifH flanking RS-1(b) resulted in hybridization, since the nifH gene is known to be highly conserved.

The foregoing method is generally applicable to the isolation of RDS's from any rhizobial species.

Rhizobial species determination using RDS probes

Applying the techniques of the foregoing Example to the cloning of RDS probes specific for each rhizobial species enables the preparation of a battery of species-specific RDS probes. Soil isolates of rhizobia are grown under laboratory culture conditions from single-colony isolates, using techniques known to those of ordinary skill in the art. The DNA of each strain is isolated and fragments thereof are obtained with the use of a restriction endonuclease, essentially as described above with respect to isolation of an RDS. The DNA fragments are fractionated by agarose gel electrophoresis as described above and probed by hybridization with a species-specific RDS probe, labelled as described in above. A positive identification of the unknown strain as belonging to a given rhizobial species will be made in the instance where an RDS probe from that species labels ("lights up") more than one band of fractionated DNA. When DNA of the unknown strain is probed with an RDS probe of a different species, there may be no hybridization of the probe to any DNA fragment or, there may be hybridization to one band if the RDS probe happens to include a region of homology with the unknown DNA flanking the RDS. It will be understood that more definitive test results will be obtained where the RDS probe includes a minimum of such flanking DNA.

Rhizobial strain determination using RDS probes

The *R. trifolii*-specific, repeated sequence probe can be used with a modified colony hybridization procedure to distinguish *R. trifolii* strains from other fast-growing rhizobial species. When used for Southern blot hybridization analysis, the probe reveals patterns of positively-hybridizing DNA fragments which characterize the Sym plasmids of different *R. trifolii* strains. The pattern of positively-hybridizing (RDS-containing) fragments is unique for a given strain, however, strains originating from similar geographical locations may possess one or more similarly-sized, RDS-containing fragments. The RDS probe represents a specific and precise diagnostic tool for the molecular taxonomy of *R. trifolii* Sym plasmids. Rhizobial strains detailed in Table 5 were obtained from Dr. A. H. Gibson. All rhizobial strains were grown on TY medium (Beringer, J. E. (1974), R factor transfer in *Rhizobium leguminosarum*, J. Gen. Microbiol. 84:188–198).

Rhizobial isolates were spotted onto TY agar and incubated for 2–3 days at 30° C. The resultant spots of growth were transferred to nitrocellulose membrane (Schleicher and Schuell, BA85) and treated with lysozyme (10 mg/ml), pronase (10 mg/ml) (Hodgson, A. L. M. and Roberts, W. P. (1983), DNA colony hybridization to identify Rhizobium strains, J. Gen. Microbiol. 129:207–212), 10% SDS (sodium dodecyl sulphate) or STET buffer (8% sucrose; 5% Triton X-100; 50 mMEDTA; 50 mM Tris-HCl, pH 8.0) (Holmes, D. S. and Quigley, M. (1981), "A rapid boiling method for the preparation of bacterial plasmids," Anal. Biochem. 114:193–197) prior to the normal colony hybridization procedure of Grunstein and Hogness (Grunstein, M. and Hogness, D. S. (1975), "Colony hybridization: a method for the isolation of cloned DNA's that contain a specific gene," Proc. Natl. Acad. Sci. USA 120:3961–3965).

TABLE 5

| | Rhizobial strains | | Symbiotic Effectiveness[a] | |
|---|---|---|---|---|
| Species | Strain | Origin | Subterranean clover | White clover |
| *R. trifolii* | CC10 | Victoria, Australia | E | E |
| | NA30 | N.S.W., Australia | E | E |
| | NN10 | N.S.W., Australia | E | — |
| | SU298[b] | N.S.W., Australia | E | I |
| | T1(162P17) | U.S.A. | — | — |
| | TA1 | Tasmania, Australia | E | E |
| | US284 | Subarctic, Sweden | — | E |
| | US2006 | Arctic, Sweden | — | E |
| | US2009 | Arctic, Sweden | — | E |
| | WA67 | W.A., Australia | E | I |

TABLE 5-continued

| | Rhizobial strains | | Symbiotic Effectiveness[a] | |
|---|---|---|---|---|
| Species | Strain | Origin | Subterranean clover | White clover |
| | WU95[c] | W.A., Australia | E | I |
| R. leguminosarum | L4(128C15) | U.S.A. | Peas | |
| | NA525(CC331) | N.S.W., Australia | Peas | |
| | TA101 | Tasmania, Australia | Peas | |
| R. phaseoli | CC511(316C15) | U.S.A. | Beans | |
| | CC365 | Brazil | Beans | |
| R. meliloti | NA39 | U.S.A. | Alfalfa | |
| | SU47 | N.S.W., Australia | Alfalfa | |

[a]E = effective, I = ineffective, — = unknown.
[b]A lysogenic strain. Its large colony-forming derivative SU843(ANU843)
[c]An unstable strain, giving rise to ineffective mutants.

Total DNA was isolated from rhizobial strains, digested with various restriction enzymes, electrophoresed on 1% agarose (SeaKem ME) gels and Southern blotted as previously described.

The R. trifolii-specific, repeated sequence (RDS) probe used was a 232 bp ClaI-AvaI restriction fragment isolated from the pBR328 recombinant plasmid pRt642, while the nifHD-specific probe was a ca 700 bp ClaI restriction fragment derived from the pBR328 recombinant plasmid pRt680. The recombinant plasmid pRt587, which consists of a 14 kb HindIII fragment carrying the R. trifolii nod genes cloned into pBR328 was used as a hybridization probe for the initial colony hybridization experiment. The RDS and nifHD-specific probe fragments were isolated by electroelution from low-melting-point agarose (SeaPlaque) gel and were radioactively labelled by random priming (Whitfeld, P. L. et al. (1982), "The human proopiomelanocortin gene: Organization, sequence, and interspersion with repetitive DNA," DNA 1:133–143). When successive probes were used on the same colony or Southern blot, the previous probe was removed by one or more 20-min. washes in 20 mM sodium hydroxide at room temperature. Complete removal of the first probe was checked by autoradiography before the second probe was applied.

The original colony hybridization procedure of Grunstein and Hogness, as developed for use with Escherichia coli, was not very effective with rhizobial isolates possibly because of poor lysis of the bacterial cells. We therefore tried various pretreatments prior to the conventional Grunstein and Hogness protocol. Four treatments were selected: lysozyme, pronase, SDS and STET buffer and were used either individually or in combination prior to the normal colony hybridization protocol. Two strains, a wild-type R. trifolii (strain ANU843) and its Sym plasmid-cured derivative (strain ANU845) were examined using the 14 kb HindIII nod gene fragment (derived from pRt587) as a hybridization probe. Bacteria were grown on TY since this medium minimizes exopolysaccharide production and thus facilitates the transfer of colonies to nitrocellulose membrane. Pronase treatment was suggested by Hodgson and Roberts, but, in our hands, this did not appear to improve subsequent cell lysis. Lysozyme did seem to improve lysis but the most satisfactory pretreatments, in terms of the final hybridization results, were those involving SDS or STET buffer. Consequently, the rhizobial colonies were pretreat lifted with 10% SDS for at least 10 min. prior to the conventional Grunstein and Hogness protocol.

Figure 2:
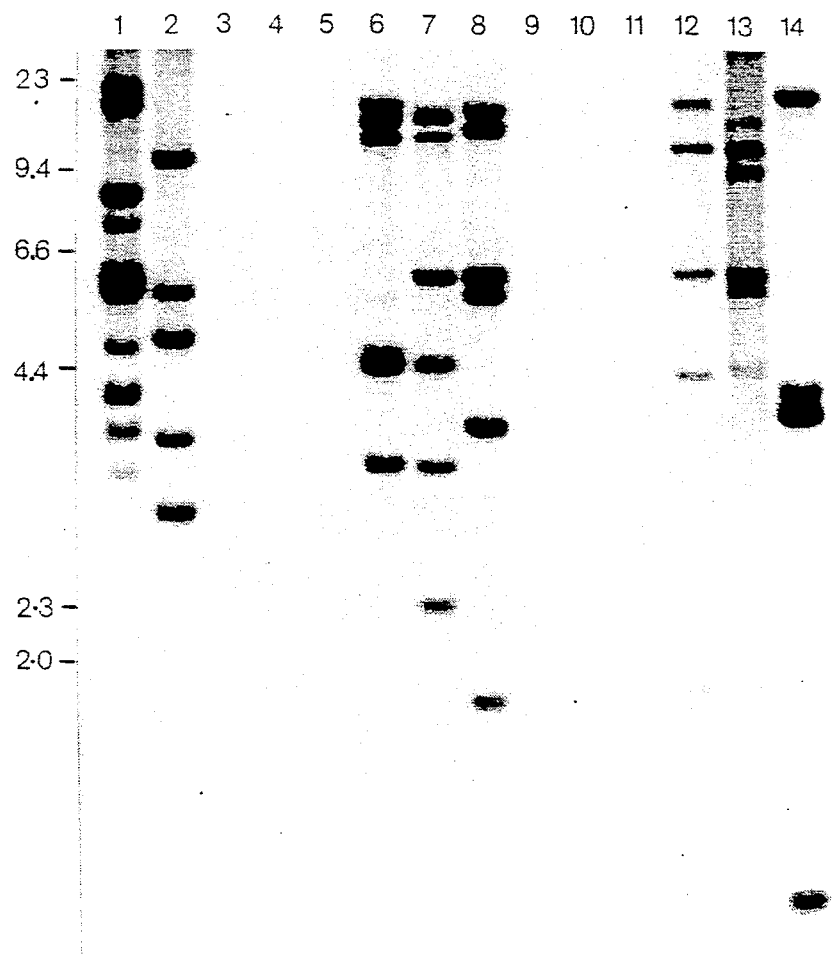
FIG. 2 shows an autoradiograph of a Southern blot of HindIII-digested DNA's derived from *R. trifolii* (Rtr), *R. leguminosarum* (Rle), *R. meliloti* (Rme) and *R. phaseoli* (Rph). Tracks: 1) Trt US2009; 2) Rtr US284; 3) Rle TA101; 4) Rme NA39; 5) Roh CC365; 6) Rtr CC10; 7) Rtr NA30; 8) Rtr SU298; 9) Rle NA525; 10) Rme SU47; 11) Rph CC511; 12) Rtr WA67; 13) Rtr WU95; 14) Rtr T1. Figures on the left indicate the relative positions of size standards (in kb) derived by HindIII digestion of bacteriophage lambda c1857 DNA.

To show that the RDS probe could be used to distinguish between isolates of R. trifolii, Southern blot hybridization analysis of total DNA derived from a number of laboratory or inoculant strains was carried out. The results of this analysis are shown in FIG. 2. Each R. trifolii strain is characterized by a unique pattern of positively-(RDS) hybridizing fragments. The numbers of such fragments in these patterns range from 4 (strain US2009) to 10 (strain T1) with the majority of patterns consisting of 5 or 6 fragments. The species specificity of the RDS probe, initially demonstrated by the colony hybridization procedure was confirmed by the Southern blot hybridization analysis. The blot shown in FIG. 2 also includes total DNA derived from strains of R. leguminosarum, R. meliloti and R. phaseoli. None of these DNA's hybridized to the RDS probe. However, when this probe was removed and the blot was hybridized with the nifHD-specific probe, each of the Rhizobium DNA's showed one or two positively-hybridizing fragments.

The R. trifolii isolates used in this study represent a range of geographically-distinct isolates. Strains CC10, NA30 and SU298 (FIG. 2, lanes 6, 7 and 8, respectively) contain one or more similarly-sized, RDS-hybridizing fragments as do strains WA67 and WU95 (FIG. 2, lanes 12 and 13, respectively). Since these two groups of strains were isolated in eastern and western Australia, respectively, it is possible that their Sym plasmids share a common evolutionary origin.

In cases where two R. trifolii strains yield very similar RDS-hybridization patterns, further taxonomic precision can be achieved by digesting the total DNA separately with different restriction enzymes. Regardless of the restriction enzyme used, the number of positively-hybridizing DNA fragments remains essentially constant. Of practical significance, however, is the fact that strains which yield related patterns when only one restriction enzyme is used (e.g. strains CC10 and NA30) are clearly distinguishable when more than one restriction enzyme is used.

Since DNA hybridization detects the presence of highly-conserved DNA sequences, the strain from which the species-specific hybridization probe is derived is irrelevant. Similar results have been obtained using the cloned nifDK promoter region from R. trifolii strain ANU794 (+TA1) as a hybridization probe. The fundamental characteristic of DNA which is revealed by Southern blot hybridization analysis is the polymorphoric distribution of restriction endonuclease sites flanking the probe sequence(s). In R. trifolii, we have shown that the enzymes HindIII, BamI, ClaI and SphI (at least) are appropriate for this type of taxonomic analysis.

The following strains and plasmids were deposited at the American Type Culture Collection, 12301 Parklawn Drive, Rockville, Md. 20852.

| Plasmid or Strain | Deposit Date | ATCC No. |
| --- | --- | --- |
| 1. E. coli RR1/pRt578 | 12/21/83 | 39545 |
| 2. E. coli RR1/pRt607 | 12/21/83 | 39546 |
| 3. E. coli RR1/pRt608 | 12/21/83 | 39547 |
| 4. E. coli RR1/pRt610 | 12/21/83 | 39548 |
| 5. E. coli RR1/pRt642 | 12/21/83 | 39549 |
| 6. pRt578 (RS-3) | 12/21/83 | 40089 |
| 7. pRt607 (RS-1(b)) | 12/21/83 | 40090 |
| 8. pRt608 (RS-1(b)) | 12/21/83 | 40091 |
| 9. pRt610 (RS-2) | 12/21/83 | 40092 |
| 10. pRt642 | 12/21/83 | 40093 |

The following bacterial strain was deposited at the Northern Regional Research Center, U.S. Department of Agriculture, 1815 North University Street, Peoria, Ill. 61604, U.S.A.:

E. coli RR1/pRt329nif-2

The date of deposit was Jun. 17, 1983, and the accession number is NRRL-B-15445.

The following plasmid was deposited with the American Type Culture Collection, 12301 Parklawn Drive, Rockville, Md. 20852, U.S.A.:

pRt329nif-2

The date of deposit was Jun. 17, 1983, and the accession number is 40072.

We claim:

1. A recombinant DNA molecule comprising:
   (a) A promoter of a nifH gene of *Rhizobium trifolii*, capable of controlling expression of a *Rhizobium trifolii* nifH gene within root nodules formed by rhizobial bacterial strains in symbiotic combination with host plants, and
   (b) a foreign structural gene under control of said promoter.

2. A recombinant DNA molecule comprising:
   (a) A promoter of a nifH gene of *Rhizobium trifolii*, capable of controlling expression of a *Rhizobium trifolii* nifH gene within root nodules formed by rhizobial bacterial strains in symbiotic combination with host plants, said promoter comprising the following sequence:

```
5'  ...  ATT  GCT  GCT  CGA  TTG  GCG  CTT  CTA  CTC  CGC  GGC  CTC  TTC  AGG
    AGC  GAC  AGA  TGT  GAC  CAG  TTG  TCG  TCA  CCT  TTG  TCG  GCT  TCG  TGA  CAC
    GCT  TTA  GGA  TTC  TTC  GGT  CCG  GTA  TTT  TAT  CCC  TCT  AAG  TGT  CTG  CGG
    CAG  CAC  CAA  CTT  CCG  TTC  TGC  CCC  TTC  AAT  CAG  CTC  AAT  TGG  CAC  GAC
    GCT  TGA  AAA  TTG  TTC  TCG  GGG  TGC  GAC  GGA  AAC  ACG  CGT  CCG  ATG  TCG
    CGG  CAT  CCC  CTC  GGT  CGA  TTC  GAA  CAC  GAA  AAG  GAA  GAA  ATA  ATG ...3'
and;
```

(b) a foreign structural gene under control of said promoter.

3. A plasmid comprising the DNA molecule of claim 1.

4. A plasmid comprising the DNA molecule of claim 2.

5. The recombinant DNA molecule of claim 1 in which the foreign structural gene is a bacterial toxin gene of *Bacillus thuringiensis*.

6. A bacterial strain comprising the DNA molecule of claim 1.

7. A bacterial strain comprising the DNA molecule of claim 2.

* * * * *